US009556246B2

(12) United States Patent
Willett

(10) Patent No.: US 9,556,246 B2
(45) Date of Patent: Jan. 31, 2017

(54) SAP VARIANTS AND THEIR USE

(71) Applicant: Promedior, Inc., Malvern, PA (US)

(72) Inventor: W. Scott Willett, Doylestown, PA (US)

(73) Assignee: Promedior, Inc., Lexington, MA (US)

(*) Notice: Subject to any disclaimer, the term of this patent is extended or adjusted under 35 U.S.C. 154(b) by 717 days.

(21) Appl. No.: 13/669,937

(22) Filed: Nov. 6, 2012

(65) Prior Publication Data

US 2013/0065838 A1  Mar. 14, 2013

Related U.S. Application Data

(63) Continuation of application No. 12/817,535, filed on Jun. 17, 2010, now Pat. No. 8,329,659.

(60) Provisional application No. 61/268,961, filed on Jun. 17, 2009.

(51) Int. Cl.
| | | |
|---|---|---|
| A61K 38/00 | (2006.01) | |
| C07K 14/47 | (2006.01) | |
| A61P 29/00 | (2006.01) | |
| A61P 27/02 | (2006.01) | |
| A61P 27/06 | (2006.01) | |
| A61K 38/17 | (2006.01) | |

(52) U.S. Cl.
CPC .......... *C07K 14/4711* (2013.01); *A61K 38/00* (2013.01); *A61K 38/17* (2013.01)

(58) Field of Classification Search
CPC ..... C07K 14/4711; A61K 38/00; A61K 38/17; A61K 45/00
See application file for complete search history.

(56) References Cited

U.S. PATENT DOCUMENTS

| | | | |
|---|---|---|---|
| 4,233,969 A | 11/1980 | Lock et al. | |
| 4,556,056 A | 12/1985 | Fischer et al. | |
| 4,782,014 A | 11/1988 | Serban et al. | |
| 5,092,876 A | 3/1992 | Dhawan et al. | |
| 5,272,258 A | 12/1993 | Siegel et al. | |
| 5,591,709 A | 1/1997 | Lindenbaum | |
| 5,654,186 A | 8/1997 | Cerami et al. | |
| 5,698,589 A | 12/1997 | Allen | |
| 5,750,345 A | 5/1998 | Bowie | |
| 5,804,446 A | 9/1998 | Cerami et al. | |
| 5,846,796 A | 12/1998 | Cerami et al. | |
| 5,989,811 A | 11/1999 | Veltri et al. | |
| 6,037,458 A | 3/2000 | Hirai et al. | |
| 6,054,121 A | 4/2000 | Cerami et al. | |
| 6,071,517 A | 6/2000 | Fanger et al. | |
| 6,126,918 A | 10/2000 | Pepys et al. | |
| 6,174,526 B1 | 1/2001 | Cerami et al. | |
| 6,365,570 B1 | 4/2002 | Van Kessel et al. | |
| 6,406,698 B1 | 6/2002 | Svehang et al. | |
| 6,537,811 B1 | 3/2003 | Freier | |
| 6,600,019 B2 | 7/2003 | Prayaga et al. | |
| 6,660,843 B1 | 12/2003 | Feige et al. | |
| 6,872,541 B2 | 3/2005 | Mills | |
| 7,666,432 B2 | 2/2010 | Gomer et al. | |
| 7,763,256 B2 | 7/2010 | Gomer et al. | |
| 8,012,472 B2 | 9/2011 | Gomer et al. | |
| 8,057,802 B2 | 11/2011 | Gomer et al. | |
| 8,187,599 B2 | 5/2012 | Gomer et al. | |
| 8,187,608 B2 | 5/2012 | Gomer et al. | |
| 8,497,243 B2 | 7/2013 | Hesson et al. | |
| 9,233,140 B2 | 1/2016 | Murray | |
| 2002/0058284 A1 | 5/2002 | Winkel | |
| 2003/0003567 A1 | 1/2003 | Barber et al. | |
| 2003/0022245 A1 | 1/2003 | Mills | |
| 2003/0162180 A1 | 8/2003 | Pricop | |
| 2004/0068095 A1 | 4/2004 | Shimkets et al. | |
| 2004/0121343 A1 | 6/2004 | Buechler et al. | |
| 2005/0182042 A1 | 8/2005 | Feldman et al. | |
| 2005/0238620 A1 | 10/2005 | Gomer et al. | |
| 2007/0048855 A1 | 3/2007 | Gamez et al. | |

(Continued)

FOREIGN PATENT DOCUMENTS

| | | |
|---|---|---|
| EP | 1 090 630 A1 | 4/2001 |
| JP | 11319542 A | 11/1999 |

(Continued)

OTHER PUBLICATIONS

Friedlander M. (2007) Fibrosis and diseases of the eye. J. Clin. Invest. 117(3):576-586.*
Banham et al., "FOXP3+ regulatory T cells: Current controversies and future perspectives," European Journal of Immunolgoy, vol. 36(11): 2832-2836 (2006).
Hori, Shohel, "Journal of Clinical and Experimental Medicine", vol. 227(5); 294-298 (2008) (abstract).
Mascarenhas, J., "Rationale for combination therapy in myelofibrosis," Best Practice & Research Clinical Haematology, vol. 27: 197-208 (2014).
Murray et al., "TGF-beta driven lung fibrosis is macrophage dependent and blocked by Serum amyloid P," The International Journal of Biochemistry & Cell Biology, vol. 43: 154-162 (2011).
Nybo et al., "Isoforms of Murine and Human Serum Amyloid P Component," Scan. J. Immunol., vol. 48: 350-356 (1998).
Schrader et al., "Animal models of dry eye," Developments in ophthalmology, vol. 41: 298-312 (2008). (Abstract).
Tanaka and Sakaguchi, "Regulatory T cell and autoimmune diseases," Japanese Journal of Clinical Immunology, vol. 28(5): 291-299 (2005).

(Continued)

*Primary Examiner* — Kimberly A. Ballard
(74) *Attorney, Agent, or Firm* — Ropes & Gray LLP

(57) ABSTRACT

Polypeptides are susceptible to denaturation or enzymatic degradation in the blood, liver or kidney. Due to the low stability of some polypeptides, it has been required to administer polypeptide drugs in a sustained frequency to a subject in order to maintain an effective plasma concentration of the active substance. Furthermore, pharmaceutical compositions of therapeutic peptides preferably have a shelf-life of several years in order to be suitable for common use. However, peptide compositions are inherently unstable due to sensitivity towards chemical and physical degradation. In part, the invention provides SAP variant proteins, compositions, pharmaceutical preparations and formulations having a prolonged in vivo half-life, prolonged shelf-life, or rather increased in vitro stability, or increased manufacturing efficiency compared to human SAP. Advantages of increased plasma half-life include, but are not limited to, reducing the amount and/or frequency of dosing.

20 Claims, 6 Drawing Sheets

(56) References Cited

U.S. PATENT DOCUMENTS

| | | |
|---|---|---|
| 2007/0065368 A1 | 3/2007 | Gomer et al. |
| 2007/0065866 A1 | 3/2007 | Gomer et al. |
| 2008/0044429 A1 | 2/2008 | Johnson et al. |
| 2009/0074754 A1 | 3/2009 | Hesson et al. |
| 2009/0074771 A1 | 3/2009 | Koenig et al. |
| 2009/0202520 A1 | 8/2009 | Lupher, Jr. et al. |
| 2010/0111898 A1 | 5/2010 | Pelura |
| 2010/0260781 A1 | 10/2010 | Murray |
| 2010/0266578 A1 | 10/2010 | Murray |
| 2010/0266643 A1 | 10/2010 | Willett |
| 2010/0317596 A1 | 12/2010 | Willett et al. |
| 2010/0323970 A1 | 12/2010 | Willett |
| 2013/0064866 A1 | 3/2013 | Willett |

FOREIGN PATENT DOCUMENTS

| | | |
|---|---|---|
| WO | WO-92/21364 A1 | 12/1992 |
| WO | WO-94/27640 A1 | 12/1994 |
| WO | WO-95/05394 A1 | 2/1995 |
| WO | WO-95/33454 | 12/1995 |
| WO | WO-97/26906 A1 | 7/1997 |
| WO | WO-99/41285 A1 | 8/1999 |
| WO | WO-99/45900 A1 | 9/1999 |
| WO | WO-01/74300 A1 | 10/2001 |
| WO | WO-03/031572 A2 | 4/2003 |
| WO | WO-03/097104 A1 | 11/2003 |
| WO | WO 2004/009823 A1 | 1/2004 |
| WO | WO-2004/016750 A2 | 2/2004 |
| WO | WO-2004/058292 A2 | 7/2004 |
| WO | WO-2004/059318 A2 | 7/2004 |
| WO | WO-2004/076486 A1 | 9/2004 |
| WO | WO-2005/110474 A2 | 11/2005 |
| WO | WO-2005/115452 A2 | 12/2005 |
| WO | WO-2006/002438 A2 | 1/2006 |
| WO | WO-2006/002930 A2 | 1/2006 |
| WO | WO-2006/028956 A2 | 3/2006 |
| WO | WO-2007/047207 A2 | 4/2007 |
| WO | WO-2007/047796 A2 | 4/2007 |
| WO | WO-2008/070117 A1 | 6/2008 |
| WO | WO-2009/009019 A2 | 1/2009 |
| WO | WO-2009/009034 A2 | 1/2009 |
| WO | WO-2010/141918 A1 | 12/2010 |

OTHER PUBLICATIONS

Ying et al., "Human Serum Amyloid P Component Oligomers Bind and Activate the Classical Complement Pathway via Residues 14-26 and 76-92 of the A Chain collagen-Like Region of C1q," J. Immunol. vol. 150(1): 169-176 (1993).

Abe, R., et al., "Peripheral Blood Fibrocytes: Differentiation Pathway and Migration to Wound Sites," The Journal of Immunology, 166(12):7556-7562 (2001).

Agostini, et al., "Chemokine/Cytokine Cocktail in Idiopathic Pulmonary Fibrosis," Proc. Am. Thorac. Soc., 3(4):357-363 (2006).

Aiba, S., et al., "Immunoglobulin-Producing Cells in Plasma Cell Orificial Mucositis," Journal of Cutaneous Pathology, 16(4):207-210 (1989).

Alles, V. V., et al., "Inducible expression of PTX3, a new member of the pentraxin family, in human mononuclear phagocytes," Blood, 84(10):3483-3493 (1994).

Ashcroft, T., et al., "Simple Method of Estimating Severity of Pulmonary Fibrosis on a Numerical Scale," J Clin Pathol, 41(4):467-470 (1988).

Ashikawa, K., et al., "Piceatannol Inhibits TNF-Induced NF-κB Activation and NF-κB-Mediated Gene Expression Through Suppression of IκBα Kinase and p65 Phosphorylation," The Journal of Immunology, 169(11):6490-6497 (2002).

Azuma, H., et al., "Superagonistic CD28 Antibody Induces Donor-Specific Tolerance in Rat Renal Allografts," American Journal of Transplantation, 8(10):2004-2014 (2008).

Bain, J., et al., "The Specificities of Protein Kinase Inhibitors: An Update," Biochem. J, 371(Pt 1):199-204 (2003).

Barna, B. P., et al., "Activation of Human Monocyte Tumoricidal Activity by C-Reactive Protein," Cancer Research, 47(5):3959-3963 (1987).

Bharadwaj et al., "Serum amyloid P component binds to Fc gamma receptors and opsonizes particles for phagocytosis," The Journal of Immunology, 166:6735-6741 (2001).

Bharadwaj, D., et al., "The Major Receptor for C-Reactive Protein on Leukocytes Is Fcγ Receptor II," The Journal of Experimental Medicine, 190(4):585-590 (1999).

Bickerstaff, M. C. M., et al., "Serum Amyloid P Component Controls Chromatin Degradation and Prevents Antinuclear Autoimmunity," Nature Medicine, 5(6):694-697 (1999).

Biro, E., et al., "Activated Complement Components and Complement Activator Molecules on the Surface of Cell-Derived Microparticles in Patients with Rheumatoid Arthritis and Healthy Individuals," Annals of the Rheumatic Diseases, 66(8):1085-1092 (2007).

Bodman-Smith, K. B., et al., "C-Reactive Protein-Mediated Phagocytosis and Phospholipase D Signalling Through the High-Affinity Receptor for Immunoglobulin G (FcγRI)," The Journal of Immunology, 107(2):252-260 (2002).

Booth, D. R., et al., Analysis of autoaggregation and ligand binding sites of serum amyloid P component by in vitro mutagenesis. From Amyloid & Amyloidosis 1998: Proceedings of the VIIIth International Symposium on Amyloidosis, Rochester, MN, pp. 23-25 (Aug. 7-11, 1998).

Boysen, S. et al., "Recombinant human serum amyloid P component from Pichia pastoris: production and characterization," Protein Expression and Purification, vol. 35(2): 284-292 (2004).

Brown, E. J., "The Role of Extracellular Matrix Proteins in the Control of Phagocytosis," Journal of Leukocyte Biology, 39(5):579-591 (1986).

Brown, M. R., et al., "Receptor-Ligand Interactions Between Serum Amyloid P Component and Model Soluble Immune Complexes," The Journal of Immunology, 151(4):2087-2095 (1993).

Bucala, R., et al., "Circulating Fibrocytes Define a New Leukocyte Subpopulation That Mediates Tissue Repair," Molecular Medicine, 1(1):71-81 (1994).

Cappiello, M. G., et al., "Suppression of IL-12 Transcription in Macrophages Following Fcγ Receptor Ligation," The Journal of Immunology, 166(7):4498-4506 (2001).

Castaño, A. P., et al., "Serum Amyloid P Inhibits Fibrosis Through FcγR-Dependent Monocyte-Macrophage Regulation in Vivo," Sci. Transl. Med. 1(5):1-26 (2009).

Chatziantoniou, et al., "Is Kidney Injury a Reversible Process," Curr. Opin. Nephrol. Hypertension, 17(1):76-81 (2008).

Chen, J., et al., "Platelet FcγRIIA His131Arg Polymorphism and Platelet Function: Antibodies to Platelet-Bound Fibrinogen Induce Platelet Activation," Journal of Thrombosis and Haemostasis, 1(2):355-362 (2003).

Chesney, J., et al., "Peripheral Blood Fibrocytes: Mesenchymal Precursor Cells and the Pathogenesis of Fibrosis," Curr. Rheumatology Reports, 2(6):501-505 (2000).

Chesney, J., et al., "Regulated Production of Type I Collagen and Inflammatory Cytokines by Peripheral Blood Fibrocytes," The Journal of Immunology, 160(1):419-425 (1998).

Chesney, J., et al., "The Peripheral Blood Fibrocyte is a Potent Antigen-Presenting Cell Capable of Priming Naive T Cells in Situ," Journal of Immunology, 94(12):6307-6312 (1997).

Chi, M., et al., "C-Reactive Protein Induces Signaling Through FcγRIIa on HL-60 Granulocytes," The Journal of Immunology, 168:1413-1418 (2002).

Christner, R. B., et al., "Binding of Human Serum Amyloid P-Component to Phosphocholine", Archives of Biochemistry and Biophysics, 314(2):337-343 (1994).

Clark, R. A. F., "Fibrin and Wound Healing," Annals New York Academy of Sciences 936:355-367 (2001).

Crouch, E., "Pathobiology of Pulmonary Fibrosis," Am J Physiol Lung Cell Mol Physiol, 259(4 Pt 1):L159-L184 (1990).

D'Andrea, A., et al., "Stimulatory and Inhibitory Effects of Interleukin (IL)-4 and IL-13 on the Production of Cytokines by

(56) References Cited

OTHER PUBLICATIONS

Human Peripheral Blood Mononuclear Cells: Priming for IL-12 and Tumor Necrosis Factor α Production," J Exp Med, 181(2):537-546 (1995).
Daëron, M., "Fc Receptor Biology," Annual Review of Immunology 15:203-234 (1997).
Daëron, M., "Structural Bases of FcγR Functions," Int Rev Immunol. 16(1-2):1-27 (1997).
De Beer, F. C., et al., "Fibronectin and C4-Binding Protein are Selectively Bound by Aggregated Amyloid Component", J Exp Med., 154(4):1134-1149 (1981).
De Beer, F. C., et al., "Isolation and Characterization of C-Reactive Protein and Serum Amyloid P Component in the Rat," Immunology 45(1):55-70 (1982).
De Beer, F. C., et al., "Isolation of Human C-Reactive Protein and serum Amyloid P Component," Journal of Immunological Methods, 50(1):17-31 (1982).
de Haas, C. J. C., et al., "A Synthetic Lipopolysaccharide-Binding Peptide Based on Amino Acids 27-39 of Serum Amyloid P Component Inhibits Lipopolysaccharide-Induced Responses in Human Blood," The Journal of Immunology, 161(7):3607-3615 (1998).
De Paepe, et al., "Hydrogels Based on Agarose and Agarose/Gelatin Blends", International Journal of Artificial Organs, vol. 24, No. 8, p. 543, XP009108972 and XXVIII Congress of the European Society for Artificial Organs on Bridging the Interdisciplinarity; Gent, Belgium; Sep. 22-25, 2001.
Du Clos, T. W., "C-Reactive Protein Reacts With the U1 Small Nuclear Ribonucleoprotein," The Journal of Immunology, 143(8):2553-2559 (1989).
Du Clos, T. W., et al., "Reply to Human C-reactive protein does not bind to FcγRIIa on phagocytic cells," The Journal of Clinical Investigation, vol. 107(5):643 (2001).
Duchemin, A. M., et al., "Association of Non-Receptor Protein Tyrosine Kinases with the FcγRI/γ Chain Complex in Monocytic Cells," The Journal of Immunology, 158(2):865-871 (1997).
Duckworth, et al., "The Structure of Agar Part I. Fractionation of a Complex Mixture of Polysaccharides," Carbohydrate Research, 16:189-197 (1971).
Emsley, J., et al., "Structure of Pentameric Human Serum Amyloid P Component," Nature 367(6461):338-345 (1994).
Flesch, B. K., et al., "The FCGR2A-Arg131 Variant is no Major Mortality Factor in the Elderly—Evidence From a German Centenarian Study," International Journal of Immunogenetics, 33(4):277-279 (2006).
Garcia de Frutos et al., "Serum Amyloid P Component Binding to C4b-binding Protein," The Journal of Biological Chemistry: 270(45):26950-26955 (1995).
Garden, A. S., et al., "Head and Neck Radiation and Mucositis," 1(1):30-34 (2007).
Gehring, et al., "Effect of Topically Applied Dexpanthenol on Epidermal Barrier Function and Stratum Corneum Hydration," Arzneim-Forsch./Drug Res., 50(11):7 (2000).
Gerhard, et al., "The Status, Quality and Expansion of the NIH Full-Length cDNA Project: The Mammalian Gene Collection (MGC)," Genome Research, 14(10B):2121-2127 (2004).
Gewurz, H., et al., "Structure and Function of the Pentraxins," Current Opinion in Immunology, 7(1):54-64 (1995).
Ghazizadeh, S., et al., "Physical and Functional Association of Src-Related Protein Tyrosine Kinases with FcγRII in Monocytic THP-1 Cells," Journal of Biological Chemistry, 269(12):8878-8884 (1994).
Giorgini, A., et al., "Blockade of Chronic Graft-VersHost Disease by Alloantigen-induced CD4+CD25+Foxp3+ Regulatory T Cells in Nonlymphopenic Hosts," Journal of Leukocyte Biology, 82(5):1053-1061 (2007).
Giri, S., et al., "Antifibrotic Effect of Decorin in a Bleomycin Hamster Model of Lung Fibrosis," Biochemical Pharmacology, 54:1205-1216 (1997).

Gregory, S. G., et al., "The DNA Sequence and Biological Annotation of Human Chromosome 1", Nature 441(7091):315-321 (2006).
Guyre, C. A., et al., "Receptor Modulation by FcγRl-Specific Fusion Proteins is Dependent on Receptor Number and Modified by IgG," The Journal of Immunology, 167(11):6303-6311 (2001).
Hamazaki, Hideaki, "Structure and significance of N-linked sugar unit of human serum amyloid P component," *Biochimica et Biophysica Acta*, 1037(3):435-438 (1990).
Harris, J. M., et al., "Pegylation a Novel Process for Modifying Pharmacokinetics," Clin. Pharmacokinetics, 40(7):539-551 (2001).
Hartlapp, I., et al., "Fibrocytes Induce an Angiogenic Phenotype in Cultured Endothelial Cells and Promote Angiogenesis in Vivo," The FASEB Journal, 15(12):2215-2224 (2001).
Heegaard, N. H. H., et al., "Ligand-Binding Sites in Human Serum Amyloid P Component," Eur. J. Biochem. 239(3):850-856 (1996).
Heegaard, N.H.H., "Microscale characterization of the structure-activity relationship of a heparin-binding glycopeptide using affinity capillary electrophoresis and immobilized enzymes," Journal of Chromatography, vol. 853(1-2):189-195 (1999).
Hicks et al., "Serum amyloid P component binds to histones and activates the classical complement pathway", The Journal of Immunology, 149:3689-3694 (1992).
Hind, C. R. K., et al., "Human Serum Amyloid P Component, a Circulating Lectin with Specificity for the Cyclic 4,6-Pyruvate Acetal of Galactose: Interactions with Various Bacteria", Biochem. J., 225(1):107-111 (1985).
Hind, C. R., et al, "Binding specificity of serum amyloid P-component for the pyruvate acetal of galactose," Journal of Experimental Medicine, 159(4):1058-1069 (1984).
Hogaboam et al., "Chronic Airway Hyperreactivity, Goblet Cell Hyperplasia, and Peribronchial Fibrosis during Allergic Airway Disease Induced by Aspergillus fumigatus," American Journal of Pathology, vol. 156(2), pp. 723-732 (2000).
Hohenester, E., et al., "Crystal Structure of a Decameric Complex of Human Serum Amyloid P Component with Bound dAMP", J. Mol. Biol. 269(4):570-578 (1997).
Huang, Z. Y., et al., "The Monocyte Fcγ Receptors FcγRI/γ and FcγRIIA Differ in their Interaction with Syk and with Src-Related Tyrosine Kinases," J Leukoc Biol 76(2):491-499 (2004).
Hundt, M., et al., "Treatment of Acute Exacerbation of Systemic Lupus Erythematosus with High-Dose Intravenous Immunoglobulin," Rheumatology (Oxford), 39(11):1301-1302 (2000).
Hutchinson, W. L., et al., "Human Serum Amyloid P Component is a Single Uncomplexed Pentamer in Whole Serum," Molecular Medicine, 6(6):482-493 (2000).
Ilium, Lisbeth, "Nasal Drug Delivery-possibilities, problems and solutions," Journal of Controlled Release, vol. 87(1-3):187-198 (2003).
Ishaque, et al., "Role of Vitamins in Determining Apoptosis and Extent of Suppression by bcl-2 During hybridoma Cell Culture," Apoptosis, 7(3):231-239 (2002).
Janeway, et al., Immunobiology, 3rd edition, Garland Publishing, pp. 3:1-3:11 (1997).
Jenny, N.S., et al., "Serum Amyloid P and Cardiovascular Disease in Older Men and Women Results from the Cardiovascular Health Study," Arterioscler. Thromb. Vasc. Biol., 27:352-358 (2007).
Junqueira, L. C.,et al., "Picrosirius Straining Plus Polarization Microscopy, A Specific Method for Collagen Detection in Tissue Sections," Histochem. J, 11(4):447-455 (1979).
Kawashima et al., Pulmonary delivery of insulin with nebulized DL-lactide/glycolide copolymer (PLGA) nanospheres to prolong hypoglycemic effect, Journal of Controlled Release, vol. 62(1-2): 279-287 (1999).
Kessel, A., et al., Intravenous Immunoglobulin Therapy Affects T Regulatory Cells by Increasing Their Suppressive Function, The Journal of Immunology, 179(8):5571-5575 (2007).
Kiernan et al., "Proteomic characterization of novel serum amyloid P component variants from human plasm and urine," Proteomics, 4:1825-1829 (2004).
Kiernan, U.A., et al., "Selected Expression Profiling of Full-Length Proteins and Their Variants from Human Plasma," Clin. Proteomics 1:7-16 (2004).

(56) References Cited

OTHER PUBLICATIONS

Kinoshita CM, et al., "A Protease-Sensitive Site in the Proposed Ca2+-Binding Region of Human Serum Amyloid Component and Other Pentraxins." Protein Sci., 1:700-709 (1992).
Kisseleva, T., et al., "Bone Marrow-Derived Fibrocytes Participate in Pathogenesis of Liver Fibrosis," Journal of Hepatology, 45(3):429-438 (2006).
Kivela-Rajamaki, M. J., et al., "Laminin-5-γ2-chain and collagenase-2 (MMP-8) in Human Peri-Implant Sulcular Fluid," Clin. Oral Implants Res., 14(2):158-165 (2003).
Kolstoe et al., "Molecular dissection of Alzheimer's disease neuropathology by depletion of serum amyloid P component", *PNAS*, 106(18):7619-7623 (2009).
Korade-Mirnics, Z.,et al., "Src Kinase-Mediated Signaling in Leukocytes," J Leukoc Biol., 68(5):603-613 (2003).
Kucuk, H. F., et al., "Effect of a Selective Cyclooxygenase-2 Inhibitor on Renal Scarring," European Surgical Research, 38(5):451-457 (2006).
Lai, J. Y., et al., "Potent Small Molecule Inhibitors of Spleen Tyrosine Kinase (Syk)," Bioorganic & Medicinal Chemistry Letters, 13(18):3111-3114 (2003).
Lei, K. K., et al., "Genomic DNA Sequence for Human C-Reactive Protein," J. Biol. Chem. 260(24):13377-13383 (1985).
Lindenbaum, E. S., et al., "Serum-Free Cell Culture Medium Induces Acceleration of Wound Healing in Guinea-Pigs," Burns, 21(2):110-115 (1995).
Liu, T., et al., "Human Plasma N-Glycoproteome Analysis by Immunoaffinity Subtraction, Hydrazide Chemistry and Mass Spectrometry," J. Proteome Res., 4(6):2070-2080 (2005).
Lu, J., et al., "Structural Recognition and Functional Activation of FcγR by Innate Pentraxins," Nature, 456(7224):989-992 (2008).
Majno, G., "Chronic Inflammation: Links With Angiogenesis and Wound Healing," American Journal of Pathology, 153(4):1035-1039 (1998).
Mantzouranis, E. C., et al., "Human Serum Amyloid P Component, cDNA Isolation, Complete Sequence of Pre-Serum Amyloid P Component, and Localization of the Gene to Chromosome 1," The Journal of Biological Chemistry, 260(12):7752-7756 (1985).
Marnell, L. L., et al., "C-Reactive Protein Binds to FcγRl in Transfected COS Cells," The Journal of Immunology, 155(4):2185-193 (1995).
Metz, C. N., "Fibrocytes: A Unique Cell Population Implicated in Wound Healing," Cell. Mol. Life Sci., 60(7):1342-1350 (2003).
Mold, C., et al., "Serum Amyloid P Component and C-Reactive Protein Mediate Phagocytosis Through Murine FcγRs," The Journal of Immunology, 166(2):1200-1205 (2001).
Moore, B. B., et al., "CCR2-Mediated Recruitment of Fibrocytes to the Alveolar Space After Fibrotic Injury," American Journal of Pathology, 166(3):675-684 (2005).
Moreira et al., "Serum amyloid P attenuates M2 macrophage activation and protects against fungal spore-induced allergic airway disease," Journal of Allergy and Clinical Immunology, vol. 126(4), pp. 712-721 (2010).
Mori, L., et al., "Fibrocytes Contribute to the Myofibroblast Population in Wounded Skin and Originate From the Bone Marrow," Exp Cell Res., 304(1):81-90 (2005).
Mortensen, R. F., et al., "Regulation of phagocytic leukocyte activities by C-reactive protein," Journal of Leukocyte Biology, 67(4):495-500 (2000).
Murphy, T. M., et al., "Extrahepatic Transcription of Human C-Reactive Protein," Journal of Experimental Medicine, 73(2):495-498 (1991).
Murray et al., "Serum amyloid P therapeutically attenuates murine bleomycin-induced pulmonary fibrosis via its effects on macrophages," PloS One, 5(3):e968 pp. 1-9 (2010).
Ohnishi, S. et al., "Isolation and Characterization of the Complete Complementary and Genomic DNA Sequences of Human Serum Amyloid P Component," J. Biochem, 100(4):849-858 (1986).
Oliveira, E. B., et al., "Primary Structure of Human C-Reactive Protein," The Journal of Biological Chemistry, 254(2):489-502 (1979).
Oriente, A., et al., "Interleukin-13 Modulates Collagen Homeostasis in Human Skin and Keloid Fibroblasts," The Journal of Pharmacology and Experimental Therapeutics, 292(3):988-994 (2000).
Osmand, A. P., et al., Partial Amino-Acid Sequences of Human and Rabbit C-Reactive Proteins: Homology with Immunoglobulins and Histocompatibility Antigens, Proc. Natl. Acad. Sci. U.S.A., 74(3):1214-1218 (1977).
Pachence, J., et al., "Tissue-Activated Delivery—Novel Methods for Site-Directed Drug Delivery," Drug Delivery Technology, 3(1):40-45 (2003).
Painter, R. H., "Evidence that C1t (Amyloid P-component) is not a subcomponent of the first component of complement (C1)," J. Immunol., 119(6):2203-2205 (1977).
Paul, William E., M.D., editor, Fundamental Immunology, 3d ed. Raven Press, p. 242 (1993).
Pepys et al., Glycobiology of Human Serum Amyloid P Component Amyloid Amyloidosis, Proc. Int. Symp. Amyloidosis, pp. 177-179 (1994).
Pepys, et al., "Targeted pharmacological depletion of serum amyloid P component for treatment of human amyloidosis", *Nature*, 471:254-259 (2002).
Pepys, et al., Human serum amyloid P component is an invariant constituent of amyloid deposits and has a uniquely homogeneous glycostructure, PNAS, 91:5206-5606 (1994).
Pepys, M. B., "Isolation of serum amyloid P-component (Protein SAP) in the Mouse," Immunology, 37(3):637-641 (1979).
Pepys, M. B., et al., "Amyloid P Component. A Critical Review," Amyloid: Int. J. Exp. Invest., 4(4):274-295 (1997).
Pepys, M. B., et al., "Serum Amyloid P Component is the Major Calcium-Dependent Specific DNA Binding Protein of Serum," Biochemical and Biophysical Research Communications, 148(1):308-313 (1987).
Pepys, MB, Serum Amyloid P. Component. Structure, Function and Role in Amlyoidosis. From Amlyoid & Amyloidosis 1998: Proceedings of the VIIIth International Symposium on Amyloidosis, Rochester, MN, pp. 6-10 (Aug. 7-11, 1998).
Philips, R. J., et al., "Circulating Fibrocytes Traffic to the Lungs in Response to CXCL 12 and Mediate Fibrosis," The Journal of Clinical Investigation, 114(3):438-446 (2004).
Pilling et al., "Aggregated IgG inhibits the differentiation of human fibrocytes," Journal of Leukocyte Biology, 79:1242-1251 (2006).
Pilling, D. et al., "Inhibition of Fibrocyte Differentiation by Serum Amyloid P.," The Journal of Immunology, 17(10):5537-5546 (2003).
Pilling, D., et al., "Reduction of Bleomycin-Induced Pulmonary Fibrosis by Serum Amyloid P," The Journal of Immunology, 179(6):4035-4044 (2007).
Pontet, M., et al., "One step preparation of both human C-reactive protein and Cit," FEBS Letters, 88(2):172-175 (1978).
Portolano et al., "Lack of Promiscuity in Autoantigen-Specific H and L Chain Combinations as Revealed by Human H and L Chain "Roulette"," J. Immunol., 150(3):880-887 (1993).
Potempa, L. A., et al., "Effect of Divalent Metal Ions and pH Upon the Binding Reactivity of Human Serum Amyloid P Component, a C-Reactive Protein Homologue, for Zymosan," The Journal of Biological Chemistry, 260(22):12142-12147 (1985).
Prelli, F., et al., "The Primary Structure of Human Tissue Amyloid P Component From a Patient with Primary Idiopathic Amyloidosis," The Journal of Biological Chemistry, 260(24):12895-12898 (1985).
Quan et al., "The role of circulating fibrocytes in fibrosis" Current Rheumatology Reports. 8(2): 145-150 (2006).
Rudikoff et al., "Single amino acid substitution altering antigen-binding specificity," Proc Natl Acad Sci USA, 79(6):1979-1983 (1982).
Rudinger, J., "Characteristics of the amino acids as components of a peptide hormone sequence," Peptide Hormones:1-7 (1975).
Russo, et al., "Liver Fibrosis; Bone Marrow Functionality Contributes to Liver Fibrosis," 130(6) Gastroenterology Week Jul. 31, 2006 pp. 83-84 (2006).

(56) References Cited

OTHER PUBLICATIONS

Russo, F. P., et al., "The Bone Marrow Functionally Contributes to Liver Fibrosis," Gastroenterology, 130(6):1807-1821 (2006).
Sada, K., et al., "Structure and Function of Syk Protein-Tyrosine Kinase," J Biochem, 130(2):177-186 (2001).
Saeland, E., at al., "Human C-reactive Protein Does not Bind to FcγRlla on Phagocytic Cells," The Journal of Clinical Investigation, 107(5):641-643 (2001).
Sawada et al., "The Ace Inhibitor, Quinapril, Ameliorates Peritoneal Fibrosis in an Encapsulating Peritoneal Sclerosis Model in Mice" Pharmacological Research. 46(6): 505-510 (2002).
Schmidt, M., et al., "Identification of Circulating Fibrocytes as Precursors of Bronchial Myofibroblasts in Asthma," The Journal of Immunology, 171(1):380-389 (2003).
Schwalbe, et al., "Pentraxin Family of Proteins Interact Specifically with Phosphorylcholine and/or Phosporylethanolamine," Biochemistry, 31:4907-1645 (1992).
Shoenfeld, Y., et al., "The mosaic of Autoimmunity: Prediction, Autoantibodies, and Therapy in Autoimmune Diseases—2008," Israel Medical Association Journal, 10(1):13-19 (2008).
Shrive, A. K., et al., "Three Dimensional Structure of Human C-Reactive Protein," Nature Structural Biology, 3(4):346-354 (1996).
Siebert et al., "Effect of enzymatic desialylation of human serum amyloid P component on surface exposure of laser photo CIDNP (chemically induced dynamic nuclear polarization)—reactive histidine, tryptophan and tyrosine residues," *FEBS Letters*, 371(1):13-16 (1995).
Siebert, Hans-Christian et al., "Comparison between intact and desialylated human serum amyloid P component by laser photo CIDNP (chemically induced dynamic nuclear polarization) technique: An indication for a conformational impact of sialic acid," Glycoconjugate Journal, vol. 14(8):945-949 (1997).
Sjoblom, T., et al., "The Consensus Coding Sequences of Human Breast and Colorectal Cancers," Science, 314(5797):268-274 (2006).
Srinivasan, N., et al., "Comparative Analyses of Pentraxins: Implications for Protomer Assembly and Ligand Binding," Structure, 2(11):1017-1027 (1994).
Steel, D. M., et al., "The Major Acute Phase Reactants: C-Reactive Protein, Serum Amyloid P Component and Serum Amyloid A Protein," Immunology Today, 15(2):81-88 (1994).
Stein, M. P., et al., "C-reactive Protein Binding to FcγRlla on Human Monocytes and Neutrophils is Allele-Specific," The Journal of Clinical Investigation, 105(3):369-376 (2000).
Su, L., et al., "Distinct Mechanisms of STAT Phosphorylation Via the Interferon-Alpha/Beta Receptor, Selective Inhibition of STAT3 and STAT5 by Piceatannol," Journal of Biological Chemistry 275(17):12661-12666 (2000).
Sutterwala, F. S., et al., "The Taming of IL-12 Suppressing the production of Proinflammatory Cytokines," Journal of Leukocyte Biology, 65(5):543-551 (1999).
Tennent et al., "Macrophage dependent elimination of amyloid following treatment with anti-SAP antibody," Amyloid: The International Journal of Experimental and Clinical Investigation, vol. 17(1); p. 51 (2010).
Thompson, A. R., et al., "Human Plasma P Component: Isolation and Characterization," Biochemistry, 17(20):4304-4311 (1978).
Thompson, D., et al., "The Physiological Structure of Human C-Reactive Protein and its Complex with Phosphocholine", Structure, 7(2):169-177 (1999).
Thomson, C. W., et al., "Lentivirally Transduced Recipient-Derived Cells to Ex Vivo Expand Functional FcRγ-Sufficient Double-Negative Regulatory T cells," Molecular Therapy, 15(4):818-824 (2007).

Toubi, E., et al., "High Dose Intravenous Immunoglobulins: An Option in the Treatment of Systemic Lupus Erythematosus," Human Immunology, 66(4):395-402 (2005).
Tridandapani, S., et al., "Regulated Expression and Inhibitory Function of Fcγ-Rllb in Human Monocytic Cells," Journal of Biological Chemistry, The American Society for Biochemistry and Molecular Biology, Inc, 277(7):5082-5089 (2002).
Trinchieri, G., "Interleukin-12 and the Regulation of Innate Resistance and Adaptive Immunity," Nature Reviews Immunology, 3(2):133-146 (2003).
Tucci, A., et al., "Biosynthesis and Postsynthetic Processing of Human C-Reactive Protein," The Journal of Immunology, 131(5):2416-2419 (1983).
Turner, M., et al., "Tyrosine Kinase SYK: Essential Functions for Immunoreceptor Signalling," Immunology Today, 21(3):148-154 (2000).
Underwood, D. C., et al., "SB 239063, A p38 MAPK Inhibitor, reduces Neutrophilia, Inflammatory Cytokines, MMP-9, and Fibrosis in Lung," Am J Physiol Lung Cell Mol Physiol, 279:L895-L902 (2000).
Volanakis, J.E., "Human C-Reactive Protein: Expression, Structure, and Function," Molecular Immunology, 38(2-3):189-197 (2001).
Wang, Q., et al., "Effect of Antibody Against Integrin α4 on Bleomycin-Induced Pulmonary Fibrosis in Mice," Biochemical Pharmacology, 60:1949-1658 (2000).
Weimann, et al., "Studies of Wound Healing: Effects of Calcium D-Panthothenate on the Migration, Proliferation and Protein Synthesis of Human Dermal Fibroblasts in Culture," Interat. J. Vit. Nutr. Res., 69(2):113-119 (1999).
Whitehead, A. S., et al., "Isolation of Human C-Reactive Protein Complementary DNA and Localization of the Gene to Chromosome 1," Science, 221(4605):69-71 (1983).
Woo, P., et al., "Characterization of Genomic and Complementary DNA Sequence of Human C-Reactive Protein, and Comparison with the Complementary DNA Sequence of Serum Amyloid P Component," The Journal of Biological Chemistry, 260(24):13384-13388 (1985).
Wynn, T. A., "IL-13 Effector Functions," Annu Rev Immunol., 2:425-456 (2003).
Yang, L., et al., "Identification of Fibrocytes in Postburn Hypertrophic Scar," Wound Repair and Regeneration, 13(4):398-404 (2005).
Yang, L., et al., "Peripheral Blood Fibrocytes From Burn Patients: Identification and Quantification of Fibrocytes in Adherent Cells Cultured From Peripheral Blood Mononuclear Cells," Laboratory Investigation, 82(9):1183-1192 (2002).
Yu, L., et al., "Therapeutic Strategies to Halt Renal Fibrosis," Current Opinion in Pharmacology, 2:177-181 (2002).
Zahedi K., "Characterization of the Binding of Serum Amyloid P to Type IV Collagen," The Journal of Biological Chemistry, 271(25):14897-14902 (1996).
Zahedi, K., "Characterization of the Binding of Serum Amyloid P to Laminin," The Journal of Biological Chemistry, 272(4):2143-2148 (1997).
Zhang, R., et al., "C-reactive Protein Impairs Human CD14(+) Monocyte-Derived Dendritic Cell Differentiation, Maturation and Function," European Journal of Immunology, 36(11):2993-3006 (2006).
Zheng, J., et al., "Piceatannol, a Stilbene Phytochemical, Inhibits Mitochondrial FOF1-ATPase Activity by Targeting the FI Complex," Biochemical and Biophysical Research Communications, 261(2):499-503 (1999).
Osmand et al., "Characterization of C-reactive protein and the complement subcomponent Clt as homologous proteins displaying cyclic pentameric symmetry (pentraxins)," PNAS, 74(2):739-743 (1977).

* cited by examiner

```
                         SEQUENCE LISTING

<160> NUMBER OF SEQ ID NOS: 2

<210> SEQ ID NO 1
<211> LENGTH: 204
<212> TYPE: PRT
<213> ORGANISM: Homo sapiens

<400> SEQUENCE: 1

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val
        195                 200

<210> SEQ ID NO 2
```

-continued

```
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: Any amino acid
<220> FEATURE:
<221> NAME/KEY: misc_feature
<222> LOCATION: (1)..(20)
<223> OTHER INFORMATION: This region may encompass 3-20 residues
<220> FEATURE:
<221> NAME/KEY: misc_feature
<222> LOCATION: (21)..(30)
<223> OTHER INFORMATION: This region may encompass 1-10 residues
<220> FEATURE:
<223> OTHER INFORMATION: See specification as filed for detailed
      description of substitutions and preferred embodiments

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Gln Gln Gln Gln Gln Gln Gln Gln Gln His Thr
            20                  25                  30

Asp Leu Ser Gly Lys Val Phe Val Phe Pro Arg Glu Ser Val Thr Asp
        35                  40                  45

His Val Asn Leu Ile Thr Pro Leu Glu Lys Pro Leu Gln Asn Phe Thr
    50                  55                  60

Leu Cys Phe Arg Ala Tyr Ser Asp Leu Ser Arg Ala Tyr Ser Leu Phe
65                  70                  75                  80

Ser Tyr Asn Thr Gln Gly Arg Asp Asn Glu Leu Leu Val Tyr Lys Glu
                85                  90                  95

Arg Val Gly Glu Tyr Ser Leu Tyr Ile Gly Arg His Lys Val Thr Ser
            100                 105                 110

Lys Val Ile Glu Lys Phe Pro Ala Pro Val His Ile Cys Val Ser Trp
        115                 120                 125

Glu Ser Ser Ser Gly Ile Ala Glu Phe Trp Ile Asn Gly Thr Pro Leu
130                 135                 140

Val Lys Lys Gly Leu Arg Gln Gly Tyr Phe Val Glu Ala Gln Pro Lys
145                 150                 155                 160

Ile Val Leu Gly Gln Glu Gln Asp Ser Tyr Gly Gly Lys Phe Asp Arg
                165                 170                 175

Ser Gln Ser Phe Val Gly Glu Ile Gly Asp Leu Tyr Met Trp Asp Ser
            180                 185                 190

Val Leu Pro Pro Glu Asn Ile Leu Ser Ala Tyr Gln Gly Thr Pro Leu
        195                 200                 205

Pro Ala Asn Ile Leu Asp Trp Gln Ala Leu Asn Tyr Glu Ile Arg Gly
    210                 215                 220

Tyr Val Ile Ile Lys Pro Leu Val Trp Val
225                 230
```

SAP VARIANTS AND THEIR USE

CROSS-REFERENCE TO RELATED APPLICATIONS

This application is a continuation of U.S. application Ser. No. 12/817,535, filed Jun. 17, 2010, which claims the benefit of U.S. Provisional Application Ser. No. 61/268,961, filed on Jun. 17, 2009. The specifications of each of the foregoing application are incorporated herein by reference in their entirety.

SEQUENCE LISTING

The instant application contains a Sequence Listing which has been submitted via EFS-Web and is hereby incorporated by reference in its entirety. The ASCII copy of the sequence listing, created on Nov. 6, 2012, is named 1041120006102_Seq.txt and is 4,618 bytes in size.

BACKGROUND OF THE INVENTION

Serum Amyloid P (SAP) is a member of the pentraxin family of proteins. SAP is secreted by the liver and circulates in the blood as a stable pentamer. Previous research demonstrates SAP has an important role in both the initiation and resolution phases of the immune response. SAP can bind to sugar residues on the surface of bacteria and thereby promote their opsonization and engulfment by antigen-presenting cells. SAP also binds to free DNA and chromatin generated by apoptotic cells at the resolution of an immune response, thus preventing a secondary inflammatory response against these antigens. Molecules bound by SAP are removed from extracellular areas due to the ability of SAP to bind to all three classical Fcγ receptors (FcγR), having a particular affinity for FcγRII (CD32) and FcγRIII (CD16). After receptor binding, SAP and any attached complex are generally internalized and processed by the cell.

Recently, it has been suggested that SAP can be used as a therapeutic agent to treat various disorders, including fibrosis-related disorders, hypersensitivity disorders, autoimmune disorders, mucositis, and inflammatory disorders such as those cause by microbial infection. See, for example, U.S. patent application Ser. Nos. 11/707,333, 12/217,617 12/720,845, and 12/720,847. Protein therapeutics for treating human disease have revolutionized the health care industry. However, there are many difficulties in producing a protein therapeutic having the necessary potency and/or in sufficient quantity to be useful as a therapeutic agent. Many potential therapeutic agents are modified to increase their biological activity, such as plasma half-life, relative to the naturally-derived protein. Recombinant expression technology is usually implemented to produce polypeptides in sufficient quantity. Unfortunately, many recombinant systems produce polypeptides having different biological properties than the naturally-derived forms, which may affect the pharmacokinetics, safety, and efficacy of a therapeutic product.

Therefore, a need remains for developing SAP polypeptides suitable for therapeutic treatment of humans.

SUMMARY OF THE INVENTION

In part, the disclosure provides Serum Amyloid P (SAP) variants and SAP oligomers. In certain aspects, the disclosure provides an SAP variant comprising five SAP protomers, wherein each of the SAP protomers have an amino acid sequence at least 90% identical to SEQ ID NO: 1, and wherein at least one of the SAP protomers comprises one or more amino acid modifications that alter a biological activity of the SAP variant compared to a corresponding sample of serum-derived human SAP. In preferred aspects, a variant SAP protomer comprises at least one amino acid modification that is characterized by the presence of one or more variant amino acids relative to SEQ ID NO: 1, the absence of one or more amino acids relative to SEQ ID NO: 1, the coupling of one or more amino acids to a modifying moiety (e.g., a PEG moiety, a dextran moiety, etc.), or a combination thereof. In some embodiments, the SAP variant is a variant of a human SAP protein. In some embodiments, one or more of the SAP protomers have an amino acid sequence at least 95%, at least 96%, at least 97%, at least 98%, at least 99%, or at least 100% identical to SEQ ID NO: 1. In preferred embodiments, SAP variants of the invention have an altered biological activity selected from one or more of increased plasma half-life, increased in vitro stability, or increased in vivo stability. In some embodiments, SAP variants of the disclosure are characterized by increased efficiency of manufacturing the SAP protein (e.g., greater yield of the protein product, increased homogeneity of the protein product, increased stability of the protein product).

In certain aspects, the disclosure provides SAP variants comprising one or more SAP protomers that are substantially free of N-linked or O-linked glycans. In some embodiments, an SAP protomer comprises an amino acid modification at position 32 of SEQ ID NO: 1 that inhibits attachment of an N-linked glycan. In some embodiments, at least one SAP protomer comprises an amino acid at position 32 of SEQ ID NO: 1 that is not asparagine (N). In preferred embodiments, at least one SAP protomer comprises an aspartate (D), glutamine (Q), or glutamate (E) at position 32 of SEQ ID NO: 1.

In certain aspects, the disclosure provides SAP variants that are more resistant to protease cleavage than a corresponding sample of serum-derived human SAP. In some embodiments, the SAP variants of the disclosure are more resistant to protease cleavage by a serine protease, a threonine proteases, a cysteine protease, an aspartic acid protease, a metalloprotease, a glutamic acid protease, or combinations thereof. In certain embodiments, the disclosure provides SAP variants that are more resistant to protease cleavage by chymotrypsin, trypsin, Pronase, or combinations thereof. In some embodiments, a protease-resistant SAP variant comprises at least one SAP protomer comprises an amino acid at position 144 of SEQ ID NO: 1 that is not phenylalanine (F). In preferred embodiments, a protease-resistant SAP variant comprises at least one SAP protomer comprising an amino acid at position 145 of SEQ ID NO: 1 that is not aspartate (D). In some embodiments, a protease resistant SAP variant comprises at least one SAP protomer comprising an amino acid at position 144 of SEQ ID NO: 1 that is not phenylalanine (F) and an amino acid at position 145 of SEQ ID NO: 1 that is not aspartate (D). In preferred embodiments, a protease-resistant SAP variant comprises at least one SAP protomer comprising a leucine (L), isoleucine (I), valine (V), or alanine (A) at position 144 of SEQ ID NO: 1. In preferred embodiments, a protease-resistant SAP variant comprises at least one SAP protomer comprising a glutamate (E) at position 145 of SEQ ID NO: 1.

In certain aspects, the disclosure provides SAP variants that are more resistant to calcium-dependent autoaggregation than a corresponding sample of serum-derived human SAP. In some embodiments, an SAP variant that is resistant to calcium-dependent autoaggregation comprises at least one SAP protomer comprising an amino acid at position 167 of SEQ ID NO: 1 that is not glutamate (E). In preferred embodiments, an SAP variant that is resistant to calcium-dependent autoaggregation comprises at least one SAP protomer comprising an aspartate (D), asparagine (N), glutamine (Q), alanine (A), or histidine (H) at position 167 of SEQ ID NO: 1.

In certain aspects, the disclosure provides SAP variants comprises at least one SAP protomer comprising one or more amino acids that are covalently attached to one or more inert polymers. In some embodiments, at least one of the inert polymers is a polyethylene glycol (PEG) moiety. In certain embodiments, one or more of the SAP protomers comprise at least one native or variant (e.g., by amino acid substitution, addition, or deletion) cysteine (C), relative to SEQ ID NO: 1, which has an attached PEG moiety. In a preferred embodiment, one or more of the SAP protomers comprise a variant cysteine (C), located at the N-terminus of SEQ ID NO: 1, which has an attached PEG moiety. In other embodiments, one or more of the SAP protomers comprise at least one native or variant (Q), relative to SEQ ID NO: 1, which has an attached PEG moiety. In a preferred embodiment, one or more of the SAP protomers comprises a glutamine (Q) at position 32 of SEQ ID NO: 1 that has an attached PEG moiety. In some embodiments, the SAP variant comprises at least one SAP protomer comprising one or more cysteine (C) residues and one or more glutamine (Q) residues that are attached to a PEG moiety. In some embodiments, at least one of the inert polymers is a dextran moiety. In certain embodiments, one or more of the SAP protomers comprises a native or variant glutamine (Q) residue, relative to SEQ ID NO: 1, which has an attached dextran moiety. In a preferred embodiment, one or more of the SAP protomers comprises an native glutamine residue at position 32 of SEQ ID NO: 1 that is has an attached dextran moiety. In certain embodiments, the SAP variant comprises at least one SAP protomer comprising one or more amino acids attached to a PEG moiety and one or more amino acids attached to a dextran moiety.

In certain aspects, the disclosure provides an SAP variant comprised of at least two, at least three, at least four, or at least five different variant SAP protomers as described herein.

In certain aspects, the disclosure provides a covalently crosslinked SAP oligomer comprising at least two SAP pentamers, wherein each of the SAP pentamers comprises five SAP protomers. SAP oligomers of the invention may comprise SAP protomers at least 90%, at least 95%, at least 96%, at least 97%, at least 98%, at least 99%, or at least 100% identical to the amino acid sequence of SEQ ID NO: 1. Accordingly, SAP oligomers of the invention may comprise at least one, at least two, at least three, at least four, at least five, at least six, at least seven, at least eight, at least nine or more of the SAP variant protomers as described herein. In some embodiments, SAP oligomers of the invention may be comprised of at least two, at least three, at least four, at least five, at least six, at least seven, at least eight, at least nine or more different variant SAP protomers as described herein. In preferred embodiments, the crosslinked SAP oligomers of the invention are characterized by one or more of increased plasma half-life, increased in vitro stability, and increased in vivo stability compared to a corresponding sample of SAP isolated from human serum.

In certain aspects, the SAP oligomers are comprised of SAP pentamers covalently attached through one or more chemical cross-linkers. In certain embodiments, at least one of the chemical cross-linker is a heterobifunctional agent selected from succinimidyl 4-(N-maleimidomethyl)cyclohexane-1-carboxylate, m-Maleimidobenzoyl-N-hydroxysuccinimide ester, N-succinimidyl (4-iodoacetyl)aminobenzoate, succinimidyl 4-(p-maleimidophenyl)butyrate, 1-ethyl-3-(3-dimethylaminopropyl)carbodiimide hydrochloride, 4-succinimidyloxycarbonyl-α-methyl-α(2-pyridyldithio)-toluene, N-succinimidyl 3-(2-pyridyldithio)propionate, or succinimidyl 6-((3-(2-pyridyldithio)propionate) hexanoate. In certain embodiments, at least one of the chemical cross-linkers is a homobifunctional agent selected from disuccinimidyl suberate, bismaleimidohexane, or dimethylpimelimidate-2HCl. In certain embodiments, at least one of the chemical cross-linkers is a photoreactive agent selected from bis-(β-(4-azidosalicylamido) ethyl)disulfide or N-succinimidyl-6-(4'-azido-2'-nitrophenyl-amino)hexanoate.

In certain aspects, the disclosure provides a pharmaceutical preparation suitable for use in a mammal comprising one or more of the SAP variants and/or covalently crosslinked SAP oligomers. Pharmaceutical preparations of the invention include at least one of the SAP variants and/or SAP oligomers disclosed herein and a pharmaceutically acceptable carrier. In some embodiments, the pharmaceutical preparation further comprises an additional active agent. In some embodiments, the pharmaceutical preparation is prepared as a sustained release formulation. In some embodiments, pharmaceutical preparations of the disclosure are suitable for administration to a patient topically, by injection, by intravenous injection, by inhalation, by continuous depot, or by pump.

The disclosure further provides methods for treating or preventing SAP-responsive disorders or conditions by administering to a patient in need thereof a therapeutically effective amount of one or more of the SAP variants and/or SAP oligomers of the invention. SAP-responsive disorders or conditions include, but are not limited to, fibrotic or fibroproliferative disorders or conditions, hypersensitivity disorders or conditions, autoimmune disorders or conditions, and mucositis. The SAP variant and/or oligomer of the invention may be administered to a patient topically, by injection, by intravenous injection, by inhalation, by continuous depot or pump, or a combination thereof. In some embodiments, the SAP variant and/or oligomer of the invention is administered conjointly with one or more additional active agents. In certain embodiments, the SAP variants and/or oligomers are formulated to be administered conjointly. The SAP variants and/or oligomers may be conjointly administered as separate or in combined formulations. The SAP variants and/or oligomers may be administered simultaneously or at different dosing schedules.

Over twenty-four hours, rates were assessed for plasma concentrations (µg/ml) of SAP protein.

Figure 3:
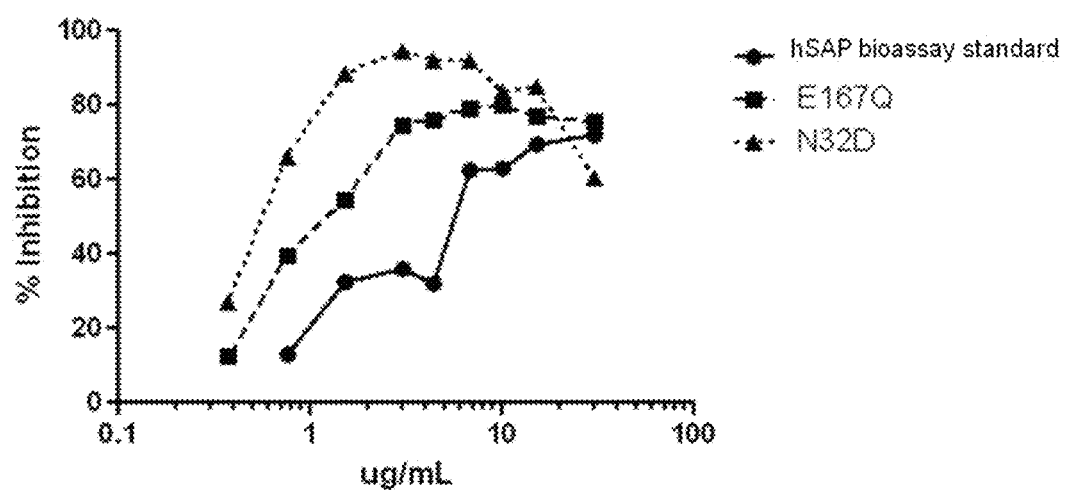

FIG. 3: SAP variants E167Q and N32D, relative to the sequence of SEQ ID NO: 1, are at least as active as a corresponding sample of unmodified recombinant human SAP (rhSAP). Monocyte-enriched Peripheral Blood Mononuclear Cells (PMBCs) were incubated with varying concentrations of SAP. Following incubation, the resulting culture supernatants were removed and assayed by ELISA to quantify the amount of Macrophage Derived Chemokine (MDC) that was produced.

Figure 4:
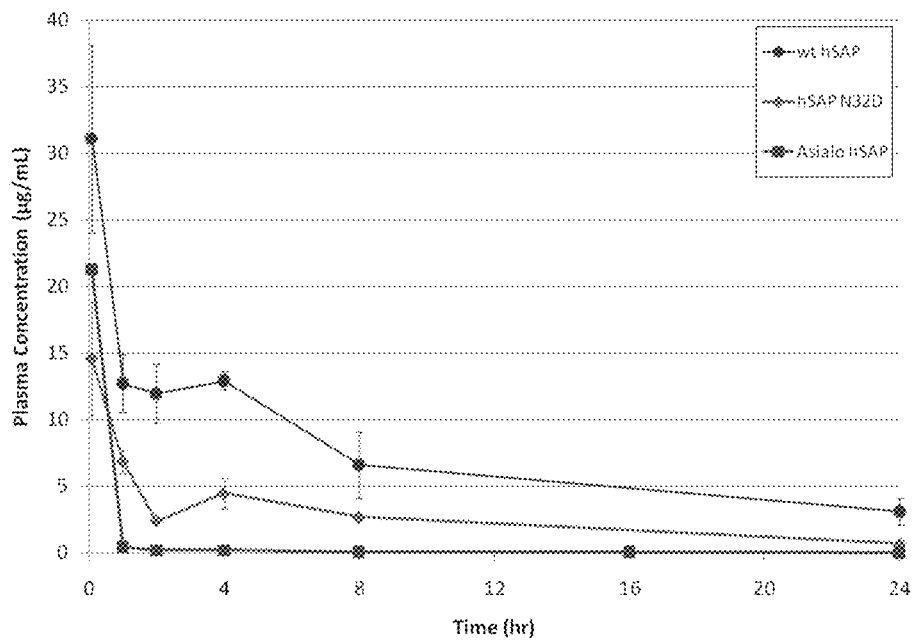

FIG. 4: The SAP variant N32D has a similar plasma half-life to that of wild-type rhSAP. While an asialo form of hSAP has a significantly reduced plasma half-life compared to a corresponding sample of unmodified recombinant human SAP (rhSAP). Rats were administered SAP (1 mg/kg i.v. does per rat, n=3). Over twenty-four hours, rates were assessed for plasma concentrations (µg/ml) of SAP protein.

Figure 5:
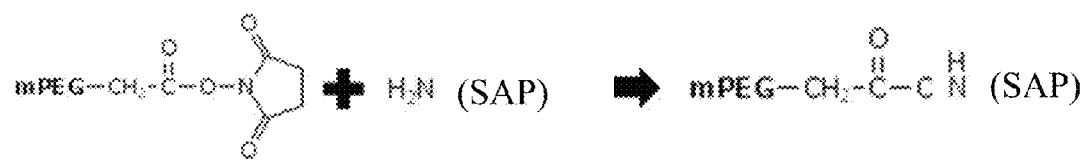

FIG. 5: Depicts a chemical reaction that covalent attaches PEG to rhSAP.

Figure 6:
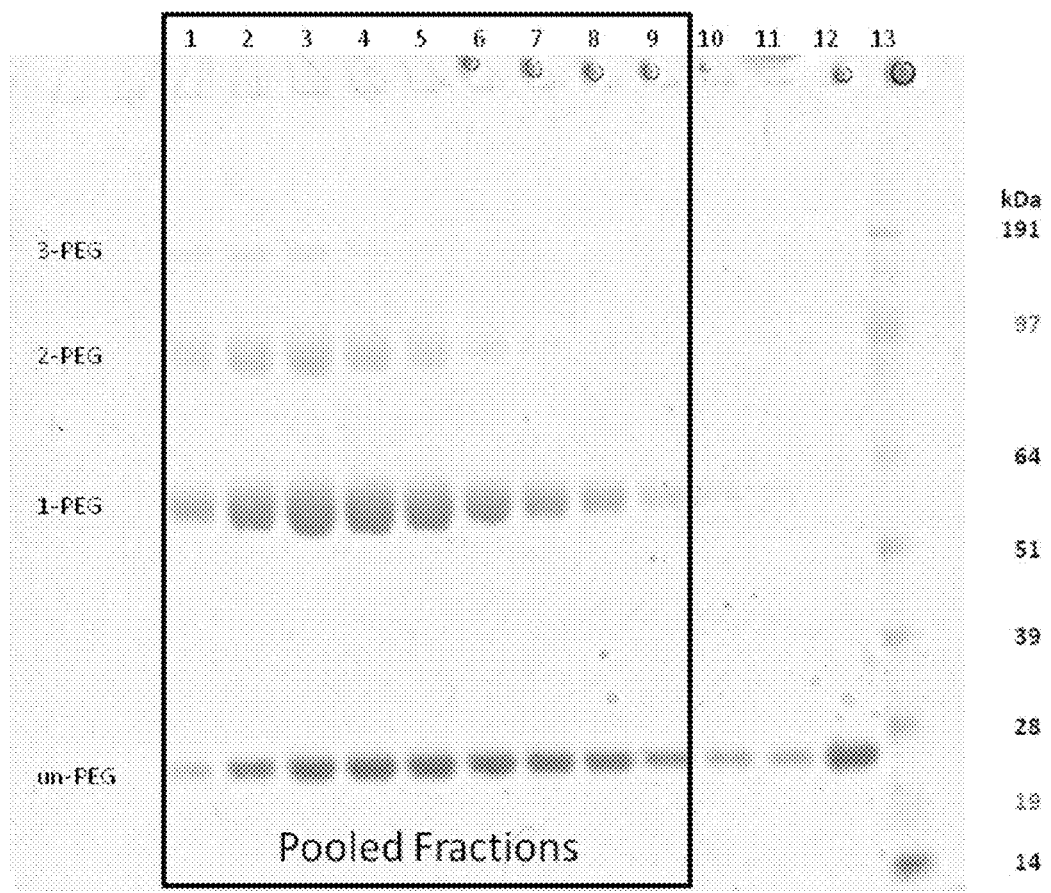

FIG. 6: Pegylated-rhSAP was purified from reaction components by anion exchange chromatography. Fractions from the chromatography column were pooled and concentrated before analysis by SDS-PAGE.

DETAILED DESCRIPTION OF THE INVENTION

Overview

Serum amyloid P ("SAP") is a naturally-occurring serum protein in mammals and is a member of the pentraxin family of structurally related proteins. It is produced in the liver as a 125,000 Dalton glycoprotein and has a physiological half-life of 24 hours in serum. SAP is composed of five identical subunits or "protomers" which are non-covalently associated in a disc-like molecule. SAP protomers non-covalently associate with each other via two "protomer interfaces". Protomer interface 1 from subunit 1 associates with protomer interface 2 from subunit 2. Protomer interface 1 from subunit 2 associates with protomer interface 2 from subunit 3, etc. Each protomer exposes an "A-face" that can bind FcγR and an opposing "B-face" that mediates calcium binding and calcium-mediated ligand binding. In high concentrations of ionic calcium, SAP aggregates and may precipitate as the amyloid P component, which is a normal constituent of glomerular basement membrane as well as human dermis, cervix, testis, and placenta tissues. See Baltz, M. L., et al., Clin. Exp. Immunol., 66:691-700 (1986); Dyck, R. F., et al., J. Exp. Med., 152:1162-1174 (1980); Melvin, T., Am. J. Pathol., 125:460-464 (1986); Breathnach, S. M., J. Invest. Derm., 92:53-58 (1989); Clayton, J., Cell. Pathol., 43:63-66 (1983); Herriut, R., et al., J. Pathol., 157:11-14 (1989); Khan, A. M., et al., Placenta, 6:551-554 (1985). The mature sequence of the human SAP protomer is depicted in below (amino acids 20-223 of Genbank Accession No. NP_001630; signal sequence not depicted).

```
                                            (SEQ ID NO: 1)
HTDLSGKVFVFPRESVTDHVNLITPLEKPLQNFTLCFRAYSDLSRAYSLF

SYNTQGRDNELLVYKERVGEYSLYIGRHKVTSKVIEKFPAPVHICVSWES

SSGIAEFWINGTPLVKKGLRQGYFVEAQPKIVLGQEQDSYGGKFDRSQSF

VGEIGDLYMWDSVLPPENILSAYQGTPLPANILDWQALNYEIRGYVIIKP

LVWV
```

Normal wound healing processes as well as the disregulated events that cause fibrosis involve the proliferation and differentiation of fibroblasts and the deposition of extracellular matrix. Whether these fibroblasts are derived locally or from a circulating precursor population is unclear. Fibrocytes, fibrocyte precursors, myofibroblast precursors, and hematopoetic monocyte precursors belong to a distinct population of fibroblast-like cells derived from peripheral blood monocytes. These cells can migrate to sites of tissue injury to promote angiogenesis and wound healing. CD14$^+$ peripheral blood monocytes cultured in the absence of serum or plasma differentiate into fibrocytes within 72 hours. Recently, SAP was shown to inhibit fibrocyte, fibrocyte precursor, myofibroblast precursor, and/or hematopoetic monocyte precursor differentiation at levels similar to that of serum. In contrast, plasma depleted of SAP has a reduced ability to inhibit differentiation of monocytes into fibrocytes, fibrocyte precursors, myofibroblast precursors, and/or hematopoetic monocyte precursors. Compared with sera from healthy individuals, serum from subjects with rheumatoid arthritis, sceleroderma, mixed connective tissue diseases, and certain systemic fibrotic diseases have reduced potency for inhibiting fibrocyte, fibrocyte precursor, myofibroblast precursor, and/or hematopoetic monocyte precursor differentiation in vitro. Accordingly, serum levels of SAP are significantly lower in some subjects with these disorders than is observed for health subjects. These results indicate that abnormally low levels of SAP may augment pathological processes leading to fibrosis and suggests SAP may be useful as a therapeutic agent to inhibit fibrosis in chronic inflammatory conditions. Recently, it has been suggested that SAP can be used as a therapeutic agent to treat various other disorders, including fibrosis-related disorders, hypersensitivity disorders, autoimmune disorders, mucositis, and inflammatory disorders such as those caused by microbial infection. See, for example, U.S. patent application Ser. Nos. 11/707,333, 12/217,617 12/720,845, and 12/720,847.

Polypeptides are susceptible to denaturation or enzymatic degradation in the blood, liver or kidney. Due to the low stability of some polypeptides, it has been required to administer polypeptide drugs in a sustained frequency to a subject in order to maintain an effective plasma concentration of the active substance. Moreover, since polypeptide drugs are usually administrated by infusion, frequent injection of polypeptide drugs may cause considerable discomfort to a subject. Thus, there have been many studies to develop polypeptide drugs that have an increased circulating half-life in the blood, while maintaining a high pharmacological efficacy. Accordingly, a primary object of the present disclosure is to provide SAP variants, compositions, pharmaceutical preparations and formulations having a prolonged in vivo half-life compared to human SAP. Advantages of increased plasma half-life include, but are not limited to, reducing the amount and/or frequency of dosing.

Furthermore, pharmaceutical compositions of therapeutic peptides preferably have a shelf-life of several years in order to be suitable for common use. However, peptide compositions are inherently unstable due to sensitivity towards chemical and physical degradation. Examples of chemical degradation include change of covalent bonds, including but not limited to, oxidation, hydrolysis, racemization, or crosslinking Examples of physical degradation include conformational changes relative to the native structure of the peptide, which may lead to aggregation, precipitation, or adsorption of the polypeptide to surfaces. Accordingly, a further object of the present disclosure is to provide SAP variants, compositions, pharmaceutical preparations and formulations that have a prolonged shelf-life, or rather increased in vitro stability, compared to human SAP. During the manufacturing process, it is often difficult to produce large quantities of a protein with reproducible consistency in the characteristics of the product, such as post-translational modification and/or folding. In some embodiments, SAP variants of the disclosure are characterized by increased efficiency of manufacturing the SAP protein (e.g., greater yield of the protein product, increased homogeneity of the protein product, increased stability of the protein product), particularly for in vivo use (e.g., as a therapeutic agent).

DEFINITIONS

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and nucleic acid chemistry and hybridization are those well known and commonly employed in the art. Standard techniques are used for nucleic acid and peptide synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, N.Y.), which are provided throughout this document.

The articles "a" and "an" are used herein to refer to one or to more than one (i.e., to at least one) of the grammatical object of the article. By way of example, "an element" means one element or more than one element.

As used herein, the terms "treatment", "treating", and the like, refer to obtaining a desired pharmacologic and/or physiologic effect. The effect may be prophylactic in terms of completely or partially preventing a disorder or symptom thereof and/or may be therapeutic in terms of a partial or complete cure for a disorder and/or adverse affect attributable to the disorder. "Treatment", as used herein, covers any treatment of a disease in a mammal, particularly in a human, and includes: (a) increasing survival time; (b) decreasing the risk of death due to the disease; (c) decreasing the risk of a disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

As used herein, a therapeutic that "inhibits" or "prevents" a disorder or condition is a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein the terms "subject" and "patient" refer to animals including mammals, such as humans. The term "mammal" includes primates, domesticated animals including dogs, cats, sheep, cattle, horses, goats, pigs, mice, rats, rabbits, guinea pigs, captive animals such as zoo animals, and wild animals.

As used herein the term "tissue" refers to an organ or set of specialized cells such as skin tissue, lung tissue, kidney tissue, and other types of cells.

The term "therapeutic effect" is art-recognized and refers to a local or systemic effect in animals, particularly mammals, and more particularly humans caused by a pharmacologically active substance. The phrase "therapeutically effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a desired effect at a reasonable benefit/risk ratio applicable to such treatment.

As used herein, the term "nucleic acid" refers to a polynucleotide such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotide.

The terms "peptides", "proteins" and "polypeptides" are used interchangeably herein. The term "purified protein" refers to a preparation of a protein or proteins that are preferably isolated from, or otherwise substantially free of, other proteins normally associated with the protein(s) in a cell or cell lysate. The term "substantially free of other cellular proteins" or "substantially free of other contaminating proteins" is defined as encompassing individual preparations of each of the proteins comprising less than 20% (by dry weight) contaminating protein, and preferably comprises less than 5% contaminating protein. Functional forms of each of the proteins can be prepared as purified preparations by using a cloned gene as is well known in the art. By "purified", it is meant that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

The term "half-life" or "plasma half-life", as used herein in the context of administering a peptide drug to a subject, is defined as the time required for plasma concentration of a drug in a subject to be reduced by one half. Further explanation of "half-life" is found in Pharmaceutical Biotechnology (1997, D F A Crommelin and R D Sindelar, eds., Harwood Publishers, Amsterdam, pp 101 120).

SAP Variants and SAP Oligomers (ii) SAP Variant Proteins

In part, the disclosure provides Serum Amyloid P (SAP) variant proteins. The term "SAP variant" is intended to refer to an SAP protein comprising five SAP subunits or "protomers". In preferred aspects, an SAP variant comprises at least one SAP protomer having one or more amino acid modifications (i.e., a variant SAP protomer) that modify at least one biological activity of the SAP protein. In some embodiments, amino acid modifications include, but are not limited to, the presence of one or more variant amino acids relative to the sequence of SEQ ID NO: 1 (e.g., amino acid substitution or addition), the absence of one or more native amino acids relative to the sequence of SEQ ID NO: 1 (e.g., amino acid deletion), the coupling of one or more amino acids to a modifying moiety (e.g., a PEG moiety, a dextran moiety, etc.), or a combination thereof. In some embodiments, an SAP protomer comprises at least one variant amino acid, relative to SEQ ID NO: 1, and at least one amino acid coupled to a modifying moiety. In particular, SAP variants of the invention are characterized by an altered biological activity compared to a corresponding sample of serum-derived human SAP. In some aspects, an SAP variant of the disclosure is characterized by an altered biological activity selected from one or more of increased plasma half-life, increased in vivo stability, increased in vitro stability, or increased manufacturing efficiency.

The term "SAP protomer" is intended to refer to a polypeptide that is at least 60%, at least 70%, at least 80%, at least 85%, at least 90%, at least 95%, at least 96%, at least 97%, at least 98%, at least 99%, or 100% identical to the SAP protomer exemplified by SEQ ID NO: 1. Accordingly, the term "SAP protomer" encompasses fragments and fusion proteins comprising any of the preceding. In preferred aspects, SAP variants of the disclosure are human SAP proteins. Generally, an SAP protomer will be designed to be soluble in aqueous solutions at biologically relevant temperatures, pH levels, and osmolarity. The protomers that non-covalently associate together to form an SAP variant of the disclosure may have identical amino acid sequences and/or post-translational modifications or, alternatively, individual protomers may have different sequences and/or modifications. Accordingly, an SAP variant may be comprised of at least two, at least three, at least four, or five identical SAP protomers or, alternatively, comprised of at least two, at least three, at least four, or at least five identical or different variant SAP protomers. In some embodiments, at least one, at least two, at least three, or at least four of the SAP protomers have 100% sequence identity to SEQ ID NO: 1. In preferred embodiments, an SAP variant comprises at least one variant SAP protomer that confers one or more altered biological activity as described herein. Post-translational modifications may be effected in vivo and/or in vitro and include, but are not limited to, processing (e.g., signal sequence removal, pro-peptide maturation, etc.) and chemical modification (e.g., glycosylation, pegylation, etc.) of the translated SAP polypeptides.

The invention also provides SAP protomers sharing a specified degree of sequence identity or similarity to an SAP polypeptide. To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, at least 40%, at least 50%, at least 60%, at least 70%, at least 80%, at least 90%, at least 95% or more of the length of a reference sequence (e.g., human SAP) is aligned for comparison purposes. The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In certain embodiments, the percent identity between two amino acid sequences is determined using the Needleman and Wunsch (J. Mol. Biol. (48):444-453 (1970)) algorithm which has been incorporated into the GAP program in the GCG software package (available at http://www.gcg.com). In a specific embodiment, the following parameters are used in the GAP program: either a Blossom 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (Devereux, J., et al., Nucleic Acids Res. 12(1):387 (1984)) (available at http://www.gcg.com). Exemplary parameters include using an NWSgapdna.CMP matrix and a gap weight of 40, 50, 60, 70, or 80 and a length weight of 1, 2, 3, 4, 5, or 6.

In another embodiment, the percent identity between two amino acid sequences is determined using the algorithm of E. Myers and W. Miller (CABIOS, 4:11-17 (1989)), which has been incorporated into the ALIGN program (version 2.0), using a PAM120 weight residue table, a gap length penalty of 12 and a gap penalty of 4.

Another embodiment for determining the best overall alignment between two amino acid sequences can be determined using the FASTDB computer program based on the algorithm of Brutlag et al. (Comp. App. Biosci., 6:237-245 (1990)). In a sequence alignment the query and subject sequences are both amino acid sequences. The result of said global sequence alignment is presented in terms of percent identity. In certain embodiments, amino acid sequence identity is performed using the FASTDB computer program based on the algorithm of Brutlag et al. (Comp. App. Biosci., 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05.

Some aspects of the invention provide SAP polypeptides (i.e., protomers), or provide therapeutic methods for employing those polypeptides, wherein said polypeptides are defined, at least in part, to a reference sequence. In preferred embodiments, the reference sequence corresponds to the amino acid sequence of SEQ ID NO: 1. Accordingly, such polypeptides may have a certain percentage of amino acid residues which are not identical to a reference sequence. In one preferred embodiment, the non-identical residues have similar chemical properties to the residues to which they are not identical. Groups that have similar properties include the following amino acids: E, D, N, and Q; H, K, and R; Y, F and W; I, L, V, M, C, and A; and S, T, C, P, and A.

In another embodiment, the residues which are not identical are those which are not evolutionarily conserved between the reference sequence and an orthologous sequence in at least one evolutionarily related species, such as in species within the same order. In the case of a mammalian reference sequence, the amino acids that may be mutated in a preferred embodiment are those that are not conserved between the reference sequence and the orthologous sequence in another mammal species. For example, if a polypeptide used in a method of the present invention is said to comprise an amino acid sequence that is at least 90% identical to human SAP (SEQ ID NO:1), then said polypeptide may have non-identical residues to those positions in which the human SAP and that of another mammal differ.

SAP polypeptides (i.e., protomers) sharing at least 90% identity with SEQ ID NO:1 include polypeptides having conservative substitutions in these areas of divergence. Typically seen as conservative substitutions are the replacements, one for another, among the aliphatic amino acids Ala, Val, Leu, and Ile, interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Additional guidance concerning which amino acid changes are likely to be phenotypically silent can be found in Bowie et al., Science 247:1306-1310 (1990).

The disclosure also provides SAP protomers with mutations in specific amino acid residues. Exemplary mutations are disclosed herein and are numbered according to the amino acid position of human SAP, e.g., as exemplified in SEQ ID NO: 1. In certain embodiments, an SAP variant i) comprises one or more protomers that are least 60%, at least 70%, at least 80%, at least 85%, at least 90%, at least 95%, at least 97%, or at least 99% identical to SEQ ID NO: 1, ii) has one or more of the following features compared to a corresponding sample of serum-derived human SAP: increased plasma half-life, increased in vitro stability, increased in vivo stability, or increased manufacturing efficiency. As described herein, amino acids of an SAP protomer may be mutated by adding one or more specified amino acid residues, deleting one or more specified amino acid residues, or substituting one or more specified amino acid residues. Methods for mutating or chemically modifying SAP polypeptides are described in the following sections.

Enhanced serum half-life and in vivo stability may be desirable to reduce the frequency of dosing that is required to achieve therapeutic effectiveness. Accordingly, in certain aspects, the serum half-life of an SAP variant is at least one, at least two, at least three, at least four, at least five, at least ten, or at least twenty days or more. Methods for pharmacokinetic analysis and determination of half-life and in vivo stability will be familiar to those skilled in the art. Details may be found in Kenneth, A et al: Chemical Stability of Pharmaceuticals: A Handbook for Pharmacists and in Peters et al, Pharmacokinetc analysis: A Practical Approach (1996). Reference is also made to "Pharmacokinetics", M Gibaldi & D Perron, published by Marcel Dekker, 2nd Rev. ex edition (1982), which describes pharmacokinetic parameters such as t alpha and t beta half lives and area under the curve (AUC). As described in the examples of the disclosure, one method for determining in vivo stability involves administering an SAP variant to an animal and measuring the concentration of the SAP variant within the plasma of the animal at regular intervals after administration. The pharmacokinetic profile (i.e. plasma concentration of SAP over time) of an SAP variant can be compared to that of another SAP protein, e.g., a corresponding sample of serum-derived human SAP.

In certain aspects, SAP variants of the disclosure are more stable than an otherwise identical composition of human SAP under identical conditions. In certain embodiments, the disclosed compositions have a shelf-life, or in vitro, stability at least two times, at least three times, at least four times, or at least five times or more as long as a corresponding sample human SAP. Many methods for measure in vitro stability are know in the art, including, for example, measuring protein stability by SDS-PAGE, Western blot, RP-HPLC, AEX-HPLC, LC-MS, or N-terminal sequencing.

In some embodiments, SAP variants of the invention have an altered or similar bioactivity compared to a corresponding sample of serum-derived human SAP. Bioactivity of an SAP variant may be determined, for example, by determining the $IC_{50}$ for inhibiting the differentiation of monocytes into fibrocytes in vitro. In some embodiments, the $IC_{50}$ of an SAP variant is less than ½, less than ⅓, less than ¼, less than ¹⁄₁₀, or less than ¹⁄₁₀₀ that of a corresponding sample of wild-type SAP isolated from human serum. There are many well characterized methods for determining the responsiveness of Peripheral Blood Mononuclear Cells (PBMCs) or monocyte cells to SAP for fibrocyte differentiation. These methods may be used to determine the relative potency of any of the SAP variant of the invention in comparison to a sample of human serum-derived SAP, any other SAP variant polypeptide, or other fibrocyte suppressant or activating agent. PBMCs or monocytes suitable for use in these methods may be obtained from various tissue culture lines. Alternatively, suitable cells for fibrocyte differentiation assays may be obtained from any biological sample that contains PBMC or monocyte cells. The biological sample may be obtained from serum, plasma, healthy tissue, or fibrotic tissue. In general, fibrocyte differentiation assays are conducted by incubating PBMC or monocyte cells in media with various concentrations of a SAP polypeptide to determine the degree of fibrocyte differentiation. The concentration of SAP can range from 0.0001 µg/mL to 1 mg/ml, and in some embodiments is 0.001 µg/mL, 1.0 µg/mL, 5 µg/mL, 10 µg/mL, 15 µg/mL, 20 µg/mL, 25 µg/mL, 30 µg/mL, 35 µg/mL, 40 µg/mL, 45 µg/mL, 50 µg/mL, 100 µg/mL, 200 µg/mL, 300 µg/mL, or 500 µg/mL. In some assays, the media can be supplemented with between 1-100 ng/ml hMCSF; the preferred concentration of hMCSF being 25 ng/mL. The indication that PBMC and monocytes have differentiated into fibrocytes can be determined by one skilled in the art. In general, fibrocytes are morphologically defined as adherent cells with an elongated spindle-shape and the presence of an oval nucleus. In some assays, cells are fixed and stained with Hema 3 before enumerating fibrocytes by direct counting, e.g., using an inverted microscope. The amount of fibrocyte differentiation is interpreted by one skilled in the art as an indication of a cell's responsiveness to SAP. As indicated by the examples of the disclosure, a greater suppression of fibrocyte differentiation indicates a greater degree of SAP responsiveness. An alternative method of measuring fibrocyte differentiation involves determining the expression of fibrocyte-specific cell surface markers or secreted factors, e.g., cytokines (such as IL-1ra, ENA-78/CXCL-5, PAI-1), fibronecctin, collagen-1, Macrophage Derived Chemokine) Methods of detecting and/or quantifying cell surface markers or secreted factors are well known in the art, including but not limited to various ELISA- and FACS-based techniques using immunoreactive antibodies against one or more fibrocyte specific markers.

In certain aspects, the disclosure provides SAP variants that are more resistant to protease cleavage than a corresponding sample of serum-derived human SAP. An SAP variant of the invention may be resistant to protease cleavage from any number of proteases including serine proteases, threonine proteases, cysteine proteases, aspartic acid proteases, metalloproteases, and glutamic acid proteases. In certain embodiments, an SAP variant is more resistant to cleavage by chymotrypsin, trypsin, or Pronase. In preferred embodiments, the protease resistant SAP variant has an increased plasma half-life compared to a corresponding sample of serum-derived human SAP. Methods for measuring proteolytic cleavage include, but are not limited to, analyzing protease-treated samples of a protein (e.g., an SAP variant and a serum-derived human SAP standard) by SDS-PAGE, Western blot, RP-HPLC, AEX-HPLC, LC-MS, or N-terminal sequencing. Other examples of protease cleavage assays are within the purview of a person skilled in the art and are exemplified in Kinoshita C M, et al., Protein Science 1:700-709 (1992). Therefore, SAP variants of the invention can readily be assayed for relative resistance to protease cleavage in comparison to a corresponding sample of another SAP protein, e.g., a sample of serum-derived human SAP.

In the absence of calcium, human SAP is susceptible to α-chymotrypin cleavage between residues $Phe_{144}$ and $Asp_{145}$ (Kinoshita C M, et. al., Protein Science 1:700-709 (1992)). In certain embodiments, an SAP protomer comprises an amino acid modification at position 144 and/or position 145 of SEQ ID NO: 1, resulting in an SAP variant that is more resistant to protease cleavage. In some embodiments, an SAP protomer comprises a variant amino acid at position 144 of SEQ ID NO: 1. In particular, SAP variants more resistant to protease cleavage may have a leucine (L), isoleucine (I), valine (V), alanine (A), or glutamine (Q) residue at amino acid position 144 of SEQ ID NO: 1. AN SAP protomer may also comprise, independently or in combination with, a variant amino acid at position 145 of SEQ ID NO: 1. Variant SAP protomers of the disclosure may comprise a glutamate (E) at position 145 at SEQ ID NO: 1. In certain embodiments, an SAP variant comprises one or more promoters that are i) at least 85%, at least 90%, at least 95%, at least 96% at least 97%, at least 98% or at least 99% identical to SEQ ID NO: 1, and ii) comprise one or more of the following amino acid substitutions F144L, F144I, F144V, F144A, F144G, D145E relative to SEQ ID NO: 1. Any of the aforementioned SAP protomers that are resistant to protease cleavage may further comprise any of the other amino acid modifications described herein.

The disclosure further provides SAP variants with increased metal-binding as compared to a corresponding sample of serum-derived human SAP. Increased metal-binding in the calcium-binding site of an SAP protomer decreases the susceptibility of the protomer to proteolysis by stabilizing the loop structure containing the amino acid residue at position 145 of SEQ ID NO: 1. In certain embodiments, an SAP variant having increased metal-binding comprises one or more SAP protomers with a variant amino acid at position 145 of SEQ ID NO: 1. In particular, SAP variants characterized by increased metal-binding may have a glutamate (E), glutamine (Q), histindine (H), alanine (A), glycine (G) amino acid at position 145 of SEQ ID NO: 1. In preferred embodiments, an SAP variant demonstrate increased metal-binding to calcium as compared to a corresponding sample of serum-derived human SAP. Calcium binding constants for an SAP protein can be measured by a variety of methods, including those exemplified in Calcium-binding Protein Protocols: methods and techniques by Hans J. Vogel, Contributor Hans J. Vogel, Published by Humana Press, 2002. In some embodiments, calcium binding constants for an SAP protein can be measured by equilibrium dialysis using a range of calcium concentrations followed by Scatchard plot analysis. (See, for example Segel, I. H., Enzyme Kinetics 1975, Wiley-Interscience Publisher, p 218-19). Equilibrium dialysis may be performed using either radioactive isotopes of calcium or calcium sensitive electrodes to quantify free calcium levels. Calcium binding constants may also be determined by titrating calcium into a solution of SAP in the presence of a chromophoric chelator (5,5'-dibromo-1,2-bis(2-aminophenoxy)ethane-N,N,N',N'-tetraacetic acid (Linse, S, Helmbersson, A. Forsen, S, 1991 JBC 266:13 pp. 8050-8054). Isothermal Titration calorimetry can also be used to measure calcium binding affinities (Wiseman, T., Williston, S., Brandts, J. F., and Lin, L. N., (1989) Anal Biochem 179, 131-7). SAP variants characterized by increased metal-binding can be compared to a corresponding sample of serum-derived human SAP for changes in proteolytic stability (e.g., digestion with chymotrypsin in the presence and absence of calcium), in vitro bioactivity and or pharmacokinetics, as well as biophysical characterization methods (e.g., RP-HPLC, SE-HPLC, SDS-PAGE, LC-MS). In certain embodiments, an SAP variant comprises one or more SAP protomers that are i) at least 85%, at least 90%, at least 95%, at least 96% at least 97%, at least 98% or at least 99% identical to SEQ ID NO: 1, and ii) comprising one or more of the following amino acid substitutions: D145E, D145Q, D145H, D145A, or D145G. Any of the aforementioned SAP protomers that demonstrate increased metal-binding may further comprise any of the other amino acid modifications described herein.

In the absence of ligand, calcium binding results in the autoaggregation of SAP (Emsley, et. al. Nature 367:338-345 (1994)), and once aggregated, SAP is rapidly cleared from the blood stream (Pepys, et. al., Nature 417:254-259 (2002)). In certain embodiments, an SAP variant of the disclosure is more resistant to calcium-dependent autoaggregation than a corresponding sample of serum-derived human SAP. In some embodiments, an SAP variant resistant to calcium-dependent autoaggregation comprises one or more SAP protomers comprising a variant amino acid at position 167 of SEQ ID NO: 1. In some embodiments, an SAP variant resistant to calcium-dependent autoaggregation comprises an aspartate (D), asparagines (N), glutamine (Q), alanine (A), or histidine (H) at position 167 of SEQ ID NO: 1. Aggregation of SAP can be determined by any number of known methods including gel filtration chromatography and dynamic light scattering (see Ho, et. al., J Biol Chem 280:31999-32008 (2005)). Therefore, SAP variants of the invention can readily be assayed for relative resistance to aggregation in comparison to a corresponding sample of another SAP protein, e.g., a sample of serum-derived human SAP. In certain embodiments, an SAP variant comprises one or more SAP protomers that are at least 85%, at least 90%, at least 95%, at least 96% at least 97%, at least 98% or at least 99% identical to SEQ ID NO: 1, and ii) comprises one or more one or more of the following amino acid substitutions: E167D, E167N, E167Q E167A, E167H. Any of the aforementioned SAP protomers that are resistant to autoaggregation may further comprise any of the other amino acid modifications described herein.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential N-linked glycosylation site. O-linked glycosylation refers to the attachment of sugar moieties (e.g., N-aceytlgalactosamine, galactose, or xylose) to a hydroxyamino acid, most commonly on a serine or threonine residue.

In certain aspects, the disclosure provides an SAP variant comprising at least one SAP protomer that is substantially free of glycans. By "substantially free" is meant that at least about 25% (e.g., at least about 27%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, or at least about 99%) of the amino acids of the SAP protomer are non-glycosylated. In preferred embodiments, an SAP protomer, or SAP variant, is free of any glycan-linked structure.

In some embodiments, SAP protomers of the disclosure have been modified to inhibit attachment of N-linked glycans, O-linked glycans or both N- and O-linked glycans. Removal of N-linked glycosylation sites on an SAP variant is accomplished by modifying (e.g., by amino acid deletion, addition or substitution) the amino acid sequence of one or more of the SAP protomers such that the protomer lacks one or more of the above-described tripeptide sequences (for N-linked glycosylation sites). The alteration may also include the deletion or substitution of one or more serine or threonine residues of the SAP protomer. In preferred embodiments, an SAP variant comprises at least one SAP protomer comprising a variant amino acid at position 32, 33, and/or 34 of SEQ ID NO: 1. In preferred embodiments, a variant SAP protomer comprises an aspartate (D), glutamine (Q), or glutamate (E) at position 32 of SEQ ID NO: 1. A variant SAP protomer may also comprise, independently or in combination with, a proline at position 33 of SEQ ID NO: 1. In certain embodiments, an SAP variant comprises one or more protomers that are i) at least 85%, at least 90%, at least 95%, at least 96% at least 97%, at least 98% or at least 99% identical to SEQ ID NO: 1, and ii) comprises one or more of the following amino acid substitutions: N32D, N32Q, N32E, 33P. Any of the aforementioned SAP protomers that are substantially free of glycans may further comprise any of the other amino acid modifications described herein.

In certain aspects, an SAP variant of the invention comprises one or more SAP protomers comprising one or more amino acid covalently attached to one or more inert polymers. An inert polymer attached to an SAP protomer may be of any effective molecular weight and may be branched or unbranched. Polymers used in the instant invention include, but are not limited to, (a) dextran and dextran derivatives, including dextran sulfate, cross-linked dextrin, and carboxymethyl dextrin; (b) cellulose and cellulose derivatives, including methylcellulose and carboxymethyl cellulose; (c) starch, cyclodextrins and dextrins, and derivatives thereof; (d) polyalkylene glycol and derivatives thereof, including PEG, mPEG, PEG homopolymers, polypropylene glycol homopolymers, copolymers of ethylene glycol with propylene glycol, wherein said homopolymers and copolymers are unsubstituted or substituted at one end with an alkyl group; (e) heparin and fragments of heparin; (f) polyvinyl alcohol and polyvinyl ethyl ethers; (g) polyvinylpyrrolidone; (h) α,β-poly((2-hydroxyethyl)-DL-aspartamide; and (i) polyoxyethylated polyols. Any of the aforementioned SAP protomers that have one or more amino acids covalently attached to one or more inert polymers may further comprise any of the amino acid modifications descried herein In preferred embodiments, the disclosure provides an SAP variant comprising one or more SAP protomers comprising at least one amino acid covalently attached to a polyethylene glycol moiety. In some embodiments, the molecular weight of a polyethylene glycol moiety is between about 1 kDa and about 100 kDa (the term "about" indicating that in preparations of polyethylene glycol, some molecules will weigh more, some less, than the stated molecular weight). Other sizes may be used, depending on the desired therapeutic profile (e.g., the duration of sustained release desired, the degree or lack of antigenicity, etc.). In certain embodiments, the polyethylene glycol may have an average molecular weight of at least 1, at least 20, or at least 40 kDa. The polyethylene glycol may have a branched structure, and branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999). Polyethylene glycol moieties may be attached to an SAP variant with consideration of effects on catalytic or targeting portions.

In preferred embodiments, the disclosure provides an SAP variant comprising one or more SAP protomers comprising at least one amino acid covalently attached to a dextran moiety. In some embodiments, the molecular weight of a dextran moiety attached to the SAP protomer is generally between about 1 kDa and about 250 kDa (the term "about" indicating that in preparations of dextran conjugates, some molecules will weigh more, some less, than the stated molecular weight). Other sizes may be used, depending on the desired therapeutic profile (e.g., the duration of sustained release desired, the degree or lack of antigenicity, etc.). In certain embodiments, the dextran may have an average molecular weight of at least 1, at least 20, or at least 40 kDa. SAP may be conjugated to dextran or a dextran derivative including dextran sulfate, p-aminoethyl cross-linked dextran, and carboxymethyl dextran.

(ii) SAP Oligomers

In certain aspects, the disclosure provides SAP oligomers comprising two or more SAP pentamers. In preferred aspects, the SAP oligomers are covalently-crosslinked pentamers, i.e., via protomer-protomer crosslinks.

There are a large number of chemical cross-linking agents that are known to those skilled in the art as well as their method of use. In certain embodiments, SAP pentamers are cross-linked using one or more heterobifunctional cross-linkers, which can be used to link proteins in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art. These include: succinimidyl 4-(N-maleimidomethyl)cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl-α-methyl-α-(2-pyridyldithio)-toluene (SMPT), N-succinimidyl 3-(2-pyridyldithio)propionate (SPDP), succinimidyl 6-((3-(2-pyridyldithio)propionate)hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exist a number of other cross-linking agents including homobifunctional and photoreactive cross-linkers. Disuccinimidyl suberate (DSS), bismaleimidohexane (BMH) and dimethylpimelimidate-2HCl (DMP) are examples of useful homobifunctional cross-linking agents, and bis-(β-(4-azidosalicylamido)ethyl)disulfide (BASED) and N-succinimidyl-6-(4'-azido-2'-nitrophenyl-amino)hexanoate (SANPAH) are examples of useful photoreactive cross-linkers for use in this invention. For a review of protein coupling techniques, see Means et al. (1990) Bioconjugate Chemistry 1:2-12.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Thiols are also particularly useful reactive groups as part of a heterobifunctional cross-linker. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds.

A third component of the heterobifunctional cross-linker is the spacer arm or bridge. The bridge is the structure that connects the two reactive ends. The most apparent feature of the bridge is its effect on steric hindrance. In some instances, a longer bridge can more easily span the distance necessary to link two complex biomolecules.

Preparing protein-protein conjugates using heterobifunctional reagents is a two-step process involving the amine reaction and the sulfhydryl reaction, and such processes are generally well known in the art. See, e.g., Partis et al. (1983) J. Pro. Chem. 2:263); Ellman et al. (1958) Arch. Biochem. Biophys. 74:443; Riddles et al. (1979) Anal. Biochem. 94:75); Blattler et al. (1985) Biochem 24:1517).

In certain aspects, the disclosure provides a covalently crosslinked SAP oligomer comprising at least two SAP pentamers, wherein each of the SAP pentamers comprises five SAP protomers. In certain embodiments, SAP oligomers of the invention may be comprised of SAP protomers at least 90%, at least 95%, at least 96%, at least 97%, at least 98%, at least 99%, or at least 100% identical to the amino acid sequence of SEQ ID NO:1. Alternatively, SAP oligomers of the invention may comprise at least one, at least two, at least three, at least four, at least five, at least six, at least seven, at least eight, at least nine or more of the variant SAP protomers described herein. In some embodiments, SAP oligomers of the invention may be comprised of at least two, at least three, at least four, at least five, at least six, at least seven, at least eight, at least nine or more different variant SAP protomers as described herein. In preferred embodiments, a crosslinked SAP oligomer of the invention is characterized by one or more of increased plasma half-life, increased in vitro stability, and increased in vivo stability compared to a corresponding sample of SAP isolated from human serum. In certain embodiments, the crosslinked SAP oligomers have one or more of the following characteristics as compared to serum-derived human SAP: increased resistance to protease, increased resistance to calcium-mediated autoaggregation, and increased metal ion-binding.

Methods of Producing SAP Variants

In part, the disclosure provides methods for generating the SAP variants and SAP oligomers of the invention. SAP variants of the disclosure may comprise at least one protomer having one or more amino acid alterations that modify at least one biological activity of the SAP protein. As described herein, methods of generating amino acid alterations include, but are not limited to, mutating at least one amino acid of SEQ ID NO: 1 (e.g., deletion of one or more amino acids, addition of one or more amino acids, or substitution of one or more amino acids), chemically modifying one or more amino acids of SEQ ID NO: 1 (e.g., attaching one or more inert polypeptides to an amino acid of SEQ ID NO: 1), or a combination thereof.

In certain aspects, variant SAP protomers of the invention may be generated using random mutagenesis techniques, directed mutagenesis techniques, directed evolution, or combination thereof. Variant SAP protomers may be generated using techniques that introduce random or directed mutations in the coding sequence of a nucleic acid. The nucleic acid is then expressed in a desired expression system, and the resulting peptide is assessed for properties of interest, e.g., resistance to autoaggregation, resistance to protease cleavage, increased metal-ion binding, increased serum half-live, increased in vitro half-life, increased in vivo half-life. Techniques to introduce random or directed mutations into DNA sequences are well known in the art, and include PCR mutagenesis, saturation mutagenesis, and degenerate oligonucleotide approaches. See Sambrook and Russell (2001, Molecular Cloning, A Laboratory Approach, Cold Spring Harbor Press, Cold Spring Harbor, N.Y.) and Ausubel et al. (2002, Current Protocols in Molecular Biology, John Wiley & Sons, NY).

In random PCR mutagenesis, reduced Taq polymerase fidelity is used to introduce random mutations into a cloned fragment of DNA (Leung et al., 1989, Technique 1:11 15). The DNA region to be mutagenized is amplified using PCR under conditions that reduce the fidelity of DNA synthesis by Taq DNA polymerase, e.g., by using an altered dGTP/dATP ratio and by adding $Mn^{2+}$ to the PCR reaction. The pool of amplified DNA fragments are inserted into appropriate cloning vectors to provide random mutant libraries.

Saturation mutagenesis allows for the rapid introduction of a large number of single base substitutions into cloned DNA fragments (Mayers et al., 1985, Science 229:242). This technique includes generation of mutations, e.g., by chemical treatment or irradiation of single-stranded DNA in vitro and synthesis of a complementary DNA strand. The mutation frequency can be modulated by modulating the severity of the treatment, and essentially all possible base substitutions can be obtained. Because this procedure does not involve a genetic selection for mutant fragments, both neutral substitutions as well as those that alter function, are obtained. Furthermore, the distribution of point mutations is not biased toward conserved sequence elements.

A library of nucleic acid homologs can also be generated from a set of degenerate oligonucleotide sequences. Chemical synthesis of a degenerate oligonucleotide sequences can be carried out in an automatic DNA synthesizer, and the synthetic genes may then be ligated into an appropriate expression vector. The synthesis of degenerate oligonucleotides is known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp. 273 289; Itakura et al. (1984) Annu Rev. Biochem. 53:323; Itakura et al. (1984) Science 198:1056; Ike et al. (1983) Nucleic Acid Res. 11:477. Such techniques have been employed in the directed evolution of other peptides (see, for example, Scott et al. (1990) Science 249:386 390; Roberts et al. (1992) PNAS 89:2429 2433; Devlin et al. (1990) Science 249: 404 406; Cwirla et al. (1990) PNAS 87: 6378 6382; as well as U.S. Pat. Nos. 5,223,409, 5,198,346, and 5,096,815).

Variant SAP protomers may also be generated using "directed evolution" techniques. These strategies are different from traditional random mutagenesis procedures because they involve subjecting the nucleic acid sequence encoding the peptide of interest to recursive rounds of mutation, screening and amplification.

In some "directed evolution" techniques, the diversity in the nucleic acids obtained is generated by mutation methods that randomly create point mutations in the nucleic acid sequence. The point mutation techniques include, but are not limited to, "error-prone PCR™" (Caldwell and Joyce, 1994; PCR Methods Appl. 2: 28 33; and Ke and Madison, 1997, Nucleic Acids Res. 25: 3371 3372), repeated oligonucle-otide-directed mutagenesis (Reidhaar-Olson et al., 1991, Methods Enzymol. 208:564 586), and any of the aforementioned methods of random mutagenesis.

Another method of creating diversity upon which directed evolution can act is the use of mutator genes. The nucleic acid of interest is cultured in a mutator cell strain the genome of which typically encodes defective DNA repair genes (U.S. Pat. No. 6,365,410; Selifonova et al., 2001, Appl. Environ. Microbiol. 67:3645 3649; Long-McGie et al., 2000, Biotech. Bioeng. 68:121 125; see, Genencor International Inc, Palo Alto, Calif.).

Achieving diversity using directed evolution techniques may also be accomplished using saturation mutagenesis along with degenerate primers (Gene Site Saturation Mutagenesis™, Diversa Corp., San Diego, Calif.). In this type of saturation mutagenesis, degenerate primers designed to cover the length of the nucleic acid sequence to be diversified are used to prime the polymerase in PCR reactions. In this manner, each codon of a coding sequence for an amino acid may be mutated to encode each of the remaining common nineteen amino acids. This technique may also be used to introduce mutations, deletions and insertions to specific regions of a nucleic acid coding sequence while leaving the rest of the nucleic acid molecule untouched. Procedures for the gene saturation technique are well known in the art, and can be found in U.S. Pat. No. 6,171,820.

Variant SAP protomers may also be generated using the techniques of gene-shuffling, motif-shuffling, exon-shuffling, and/or codon-shuffling (collectively referred to as "DNA shuffling"). DNA shuffling techniques are may be employed to modulate the activities of peptides useful in the invention and may be used to generate peptides having altered activity. See, generally, U.S. Pat. Nos. 5,605,793; 5,811,238; 5,830,721; 5,834,252; and 5,837,458, and Stemmer et al. (1994, Nature 370(6488):389 391); Crameri et al. (1998, Nature 391 (6664):288 291); Zhang et al. (1997, Proc. Natl. Acad. Sci. USA 94(9):4504 4509); Stemmer et al. (1994, Proc. Natl. Acad. Sci. USA 91(22):10747 10751); Patten et al. (1997, Curr. Opinion Biotechnol. 8:724 33); Harayama, (1998, Trends Biotechnol. 16(2):76 82); Hansson, et al., (1999, J. Mol. Biol. 287:265 76); and Lorenzo and Blasco (1998, Biotechniques 24(2):308 13) Each of these are hereby incorporated by reference in their entirety.

DNA shuffling involves the assembly of two or more DNA segments by homologous or site-specific recombination to generate variation in the polynucleotide sequence. DNA shuffling has been used to generate novel variations of human immunodeficiency virus type 1 proteins (Pekrun et al., 2002, J. Virol. 76(6):2924 35), triazine hydrolases (Raillard et al. 2001, Chem Biol 8(9):891 898), murine leukemia virus (MLV) proteins (Powell et al. 2000, Nat Biotechnol 18(12):1279 1282), and indoleglycerol phosphate synthase (Merz et al. 2000, Biochemistry 39(5):880 889).

The technique of DNA shuffling was developed to generate biomolecular diversity by mimicking natural recombination by allowing in vitro homologous recombination of DNA (Stemmler, 1994, Nature 370: 389 391; and Stemmler, 1994, PNAS 91: 10747 10751). Generally, in this method a population of related genes is fragmented and subjected to recursive cycles of denaturation, rehybridization, followed by the extension of the 5' overhangs by Taq polymerase. With each cycle, the length of the fragments increases, and DNA recombination occurs when fragments originating from different genes hybridize to each other. The initial fragmentation of the DNA is usually accomplished by nuclease digestion, typically using DNase (see Stemmler references, above), but may also be accomplished by interrupted PCR synthesis (U.S. Pat. No. 5,965,408, incorporated herein by reference in its entirety; see, Diversa Corp., San Diego, Calif.). DNA shuffling methods have advantages over random point mutation methods in that direct recombination of beneficial mutations generated by each round of shuffling is achieved and there is therefore a self-selection for improved phenotypes of peptides. The techniques of DNA shuffling are well known to those in art. Detailed explanations of such technology is found in Stemmler, 1994, Nature 370: 389 391 and Stemmler, 1994, PNAS 91: 10747 10751. The DNA shuffling technique is also described in U.S. Pat. Nos. 6,180,406, 6,165,793, 6,132,970, 6,117,679, 6,096,548, 5,837,458, 5,834,252, 5,830,721, 5,811,238, and 5,605,793. Each of these are hereby incorporated by reference in their entirety.

The art also provides even more recent modifications of the basic technique of DNA shuffling. In one example, exon shuffling, exons or combinations of exons that encode specific domains of peptides are amplified using chimeric oligonucleotides. The amplified molecules are then recombined by self-priming PCR assembly (Kolkman and Stemmler, 2001, Nat. Biotech. 19:423 428). In another example, using the technique of random chimeragenesis on transient templates (RACHITT) library construction, single stranded parental DNA fragments are annealed onto a full-length single-stranded template (Coco et al., 2001, Nat. Biotechnol. 19:354 359). In yet another example, staggered extension process (StEP), thermocycling with very abbreviated annealing/extension cycles is employed to repeatedly interrupt DNA polymerization from flanking primers (Zhao et al., 1998, Nat. Biotechnol. 16: 258 261). In the technique known as CLERY, in vitro family shuffling is combined with in vivo homologous recombination in yeast (Abecassis et al., 2000, Nucleic Acids Res. 28:E88). To maximize intergenic recombination, single stranded DNA from complementary strands of each of the nucleic acids are digested with DNase and annealed (Kikuchi et al., 2000, Gene 243:133 137). The blunt ends of two truncated nucleic acids of variable lengths that are linked by a cleavable sequence are then ligated to generate gene fusion without homologous recombination (Sieber et al., 2001, Nat. Biotechnol. 19:456 460; Lutz et al., 2001, Nucleic Acids Res. 29:E16; Ostermeier et al., 1999, Nat. Biotechnol. 17:1205 1209; Lutz and Benkovic, 2000, Curr. Opin. Biotechnol. 11:319 324). Recombination between nucleic acids with little sequence homology in common has also been enhanced using exonuclease-mediated blunt-ending of DNA fragments and ligating the fragments together to recombine them (U.S. Pat. No. 6,361,974, incorporated herein by reference in its entirety).

In addition to published protocols detailing directed evolution and gene shuffling techniques, commercial services are now available that will undertake the gene shuffling and selection procedures on peptides of choice. Maxygen (Redwood City, Calif.) offers commercial services to generate custom DNA shuffled libraries. In addition, this company will perform customized directed evolution procedures including gene shuffling and selection on a peptide family of choice.

Optigenix, Inc. (Newark, Del.) offers the related service of plasmid shuffling. Optigenix uses families of genes to obtain mutants therein having new properties. The nucleic acid of interest is cloned into a plasmid in an *Aspergillus* expression system. The DNA of the related family is then introduced into the expression system and recombination in conserved regions of the family occurs in the host. Resulting mutant DNAs are then expressed and the peptide produced therefrom are screened for the presence of desired properties and the absence of undesired properties.

Following each recursive round of "evolution," the desired peptides expressed by mutated genes are screened for characteristics of interest. The "candidate" genes are then amplified and pooled for the next round of DNA shuffling. The screening procedure used is highly dependant on the peptide that is being "evolved" and the characteristic of interest. Characteristics such as peptide stability, biological activity, antigenicity, among others can be selected using procedures that are well known in the art.

It will be appreciated by the skilled artisan that the above techniques of mutation and selection can be combined with each other and with additional procedures to generate the best possible variant SAP protomer useful in the methods of the invention. Thus, the invention is not limited to any one method for the generation of SAP variants, and should be construed to encompass any and all of the methodology described herein. For example, a procedure for introducing specified point mutations into a nucleic acid sequence may be performed initially, followed by recursive rounds of DNA shuffling, selection and amplification. For some variants the initial introduction of point mutations may be used to introduce diversity into a gene population where it is lacking, and the following round of DNA shuffling and screening will select for advantageous point mutations.

In certain aspects, the disclosure provides methods for chemically modifying one or more amino acids of an SAP protomer. There are a number of methods described in the art for attaching inert polymers to a polypeptide including, but not limited to, using cyanogen bromide (alkylation) and dialdehyde coupling chemistry and periodate oxidation. In particular, many methods for pegylating amino acids have been described in the art. For example, U.S. Pat. No. 4,088,538 discloses an enzymatically active polymer-enzyme conjugate of an enzyme covalently bound to PEG. Similarly, U.S. Pat. No. 4,496,689 discloses a covalently attached complex of α-1 protease inhibitor with a polymer such as PEG or methoxypoly(ethylene glycol) ("mPEG"). Abuchowski et al. (J. Biol. Chem. 252: 3578 (1977) discloses the covalent attachment of mPEG to an amine group of bovine serum albumin. U.S. Pat. No. 4,414,147 discloses a method of rendering interferon less hydrophobic by conjugating it to an anhydride of a dicarboxylic acid, such as poly(ethylene succinic anhydride). PCT WO 87/00056 discloses conjugation of PEG and polyoxyethylated polyols to such proteins as interferon-β, interleukin-2 and immunotoxins. EP 154,316 discloses and claims chemically modified lymphokines, such as IL-2 containing PEG bonded directly to at least one primary amino group of the lymphokine U.S. Pat. No. 4,055,635 discloses pharmaceutical compositions of a water-soluble complex of a proteolytic enzyme linked covalently to a polymeric substance such as a polysaccharide. Another mode of attaching PEG to peptides is through the non-specific oxidation of glycosyl residues on a peptide. The oxidized sugar is utilized as a locus for attaching a PEG moiety to the peptide. For example WO 94/05332 discloses the use of a hydrazine- or amino-PEG to add PEG to a glycoprotein. The glycosyl moieties are randomly oxidized to the corresponding aldehydes, which are subsequently coupled to the amino-PEG.

The disclosure also provides SAP variants comprising site-specific pegylation. In some embodiments, an SAP protomer is modified by the introduction of a "free" cysteine residues (i.e., cysteines that are not involved in disulfide bonds) to which PEG can be attached using well described malaimide chemistry. (See, e.g., Natarajan, Bioconjug Chem. 2005 January-February; 16(1): 113-21; Goodson, Biotechnology NY. 1990 April; 8(4):343-6). Modified SAP variants are provided, wherein polymer conjugation sites are introduced via variant cysteine residues. The cysteine residue may be substituted for one or more native SAP amino acid residues or by adding one or more cysteines to an SAP polypeptide. In some embodiments, a cysteine residue is introduced at position −1 of SEQ ID NO: 1 (i.e., added to the N-terminus of the polypeptide). In some embodiments, a cysteine residue in introduced by the substitution of the native amino acid a position 32 of SEQ ID NO: 1 for a cysteine residue. In some embodiments, the introduced cysteine is pegylated.

For pegylation of cysteine residues, the polypeptide may be treated with a reducing agent, such as dithiothreitol (DDT) prior to pegylation. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to about 16 hours. Examples of activated PEG polymers for coupling to cysteine residues include the following linear and branched PEGs, including but not limited to, vinylsulfone-PEG (PEG-VS), such as vinylsulfone-mPEG (mPEG-VS); orthopyridyl-disulfide-PEG (PEG-OPSS), such as orthopyridyl-disulfide-mPEG (MPEG-OPSS); and maleimide-PEG (PEG-MAL), such as maleimide-mPEG (mPEG-MAL) and branched maleimide-mPEG2 (mPEG2-MAL).

One approach for adding PEG or dextran to SAP utilizes the enzyme transglutaminase (glutamyl-peptide γ-glutamyltransferase; EC 2.3.2.13). This enzyme catalyzes the calcium-dependent acyl addition to a primary amine wherein the gamma-carboxamide group of peptide-bound glutamine residue is the acyl donor and the primary amine is the acyl acceptor and amine donor. A transglutaminase reaction is therefore employed to covalently and site-specifically conjugate SAP to a polymer, such as PEG or dextran through a Gln residue that is capable of acting as a transglutaminase amine acceptor.

The transglutaminase amine acceptor in SAP may be an native or introduced (i.e., variant) Gln residue. In general, glutamine repeats have been shown to enhance the acceptor properties of each glutamine residue in the repeat, and the accessibility of glutamine residues has also been shown to be important in determining their ability to function as transglutaminase substrates (Kahlem, P. et al. Proc. Natl. Acad. Sci. USA 1996, 93, 14580-14585). In some embodiments, the SAP variant comprises an N32Q mutation, introducing a transglutaminase amine acceptor. In some embodiments, the SAP variant comprises the amino acid sequence at least 70, 80, 85, 90, 95, 98, or 100% identical to SEQ ID NO: 2 (wherein X is any amino acid, $_A$ is 3 to 20, and $_Y$ is 1 to 10):

(SEQ ID NO: 2)
X$_A$Q$_Y$HTDLSGKVFVFPRESVTDHVNLITPLEKPLQNFTLCFRAYSDLSRA

YSLFSYNTQGRDNELLVYKERVGEYSLYIGRHKVTSKVIEKFPAPVHICV

SWESSSGIAEFWINGTPLVKKGLRQGYFVEAQPKIVLGQEQDSYGGKFDR

SQSFVGEIGDLYMWDSVLPPENILSAYQGTPLPANILDWQALNYEIRGYV

IIKPLVWV

In some embodiments, $_Y$ is 1. In some embodiments, $_Y$ is 2. In some embodiments, the SAP variant is conjugated to PEG via a transglutaminase amine acceptor. In some embodiments, the SAP variant is conjugated to dextran via a transglutaminase amine acceptor.

Methods for adding polymers to Gln residues have been described in the art (See, e.g., U.S. Publication No. 20060116322, Sugimura et al. 281 (26): 17699. (2006); Sato, H. Adv Drug Deliv Rev. 2002 Jun. 17; 54(4):487-504; Sato, et al, Bioconjug Chem. 2000 July-August; 11(4):502-9; Sato, et al Bioconjug Chem. 2001 September-October; 12(5):701-10, Fontana, et al Adv Drug Deliv Rev. 2008 Jan. 3; 60(1):13-28. Epub 2007 Aug. 16, Hohenadl, J Biol. Chem. 1995 Oct. 6; 270(40):23415-20)). The polymers are linked or modified to contain a primary amine which will act as the transglutaminase amine donor.

SAP variants and SAP covalently crosslinked oligomers described herein may be produced in bacterial cells, insect cells, yeast, fungal cells, or mammalian cells including, for example, human cells. In those instances when the host cell is human, the cell may be in a live subject or may be isolated from a subject, e.g., in a cell culture, tissue sample, cell suspension, etc. Other suitable host cells are known to those skilled in the art.

The disclosure further provides expression vectors for producing SAP protomers. For instance, expression vectors are contemplated which include a nucleotide sequence encoding an SAP protomer, wherein the coding sequence is operably linked to at least one transcriptional regulatory sequence. Regulatory sequences for directing expression of SAP protomers are art-recognized and are selected by a number of well understood criteria. Exemplary regulatory sequences are described in Goeddel; Gene Expression Technology: Methods in Enzymology, Academic Press, San Diego, Calif. (1990). For instance, any of a wide variety of regulatory sequences that control the expression of a DNA sequence when operatively linked to it may be used in these vectors to express DNA sequences encoding SAP protomers. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the promoter for 3-phosphoglycerate kinase or other glycolytic enzymes, the promoters of acid phosphatase, e.g., Pho5, and the promoters of the yeast α-mating factors and other sequences known to control the expression of genes of prokaryotic or eukaryotic cells or their viruses, and various combinations thereof. It should be understood that the design of the expression vector may depend on such factors as the choice of the target host cell to be transformed. Moreover, the vector's copy number, the ability to control that copy number and the expression of any other protein encoded by the vector, such as antibiotic markers, should also be considered.

The disclosure also provides a host cell transfected with a recombinant gene in order to express an SAP protomer. The host cell may be any prokaryotic or eukaryotic cell. For example, an SAP protomer may be expressed in bacterial cells such as E. coli, insect cells, yeast, or mammalian cells. Other suitable host cells are known to those skilled in the art.

Accordingly, the disclosure provides methods of producing SAP protomers. For example, a host cell transfected with an expression vector encoding an SAP protomer of the invention can be cultured under appropriate conditions to allow expression of the polypeptide to occur. The SAP protomer may be secreted, by inclusion of a secretion signal sequence, and isolated from a mixture of cells and medium containing the protein. Alternatively, the SAP protomer may be retained cytoplasmically and the cells harvested, lysed and the protomer isolated. A cell culture includes host cells, media and other byproducts. Suitable media for cell culture are well known in the art. The proteins can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the protein.

Thus, a coding sequence for an SAP protomer can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures.

Expression vehicles for production of a recombinant protein include plasmids and other vectors. For instance, suitable vectors for the expression of SAP protomers include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEp24, YIp5, YEp51, YEp52, pYES2, and YRp17 are cloning and expression vehicles useful in the introduction of genetic constructs into S. cerevisiae (see, for example, Broach et al., (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. Autotrophic selection or counterselection is often used in yeast. In addition, drug resistance markers, such as ampicillin, can be used in bacteria.

Mammalian expression vectors may contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant SAP polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the beta-gal containing pBlueBac III).

In some instances it will be desired to produce SAP protomers in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59. (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; a human hepatoma line (Hep G2); and myeloma or lymphoma cells (e.g. Y0, J558L, P3 and NS0 cells) (see U.S. Pat. No. 5,807,715).

In certain embodiments, production of SAP protomers may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

Often, it is difficult to produce large quantities of a protein with reproducible consistency in the characteristics of the product, such as post-translational modification and/or folding. In some embodiments, SAP variants of the disclosure are characterized by increased efficiency of manufacturing the SAP protein (e.g., greater yield of the protein product, increased homogeneity of the protein product, increased stability of the protein product), particularly for in vivo use (e.g., as a therapeutic agent). In some embodiments, SAP variants of the disclosure are characterized by increased stability and/or homogeneity when expressed in a cell (e.g., prokaryote, eukaryote) compared to wild-type SAP expressed in the same cell line. For example, recombinant proteins are generally characterized by a high degree of heterogeneity with regards to their attached glycan structures. SAP variants having a modified amino acid sequence to inhibit glycoslyation (such as an amino acid substitution at position 32 of SEQ ID NO: 1, e.g., N32D) would be expected to be more homogenously produced from a cell.

In exemplary embodiments, SAP variants, may be purified, for example, to at 80%, 85%, 90%, 95%, 98%, 99%, or 99.9% purity, or greater, with respect to contaminating macromolecules, particularly other proteins and nucleic acids, and free of infectious and pyrogenic agents. SAP variants may be substantially free of other polypeptides, particularly other polypeptides of animal origin.

SAP variants can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are suitable, including, for example, DEAE Fast-Flow Sepharose (Pharmacia, Piscataway, N.J.). Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding polypeptides to support media are well known in the art. Selection of a particular method is a matter of routine design and is determined in part by the properties of the chosen support. See, for example, Affinity Chromatography Principles & Methods (Pharmacia LKB Biotechnology, Uppsala, Sweden, 1988). The SAP variants described herein can also be isolated an affinity tag (e.g., polyhistidine, maltose-binding protein, GST, starch binding domain, FLAG, an immunoglobulin domain) to facilitate purification as described further herein.

Treatment Methods

In certain aspects, the disclosure provides methods for treating an SAP-responsive disorder in a patient by administering a therapeutically effective amount of an SAP variant or SAP oligomer of the invention to a patient in need thereof. The dosage and frequency of treatment can be determined by one skilled in the art and will vary depending on the symptoms, age and body weight of the patient, and the nature and severity of the disorder to be treated or prevented. In some embodiments, an SAP variant or SAP oligomer is administered to a patient once or twice per day, once or twice per week, once or twice per month, or just prior to or at the onset of symptoms.

Dosages may be readily determined by techniques known to those of skill in the art or as taught herein. Toxicity and therapeutic efficacy of SAP may be determined by standard pharmaceutical procedures in experimental animals, for example, determining the $LD_{50}$ and the $ED_{50}$. The $ED_{50}$ (Effective Dose 50) is the amount of drug required to produce a specified effect in 50% of an animal population. The $LD_{50}$ (Lethal Dose 50) is the dose of drug which kills 50% of a sample population.

In some embodiments, the SAP-responsive disorder is fibrosis. The use of SAP as a therapeutic treatment for fibrosis is described in U.S. Patent Application No. 2007/0243163, which is hereby incorporated by reference. Fibrosis related disorders that may be amenable to treatment with the subject method include, but are not limited to, collagen disease, interstitial lung disease, human fibrotic lung disease (e.g., obliterative bronchiolitis, idiopathic pulmonary fibrosis, pulmonary fibrosis from a known etiology, tumor stroma in lung disease, systemic sclerosis affecting the lungs, Hermansky-Pudlak syndrome, coal worker's pneumoconiosis, asbestosis, silicosis, chronic pulmonary hypertension, AIDS-associated pulmonary hypertension, sarcoidosis, moderate to severe asthma and the like), fibrotic vascular disease, arterial sclerosis, atherosclerosis, varicose veins, coronary infarcts, cerebral infarcts, myocardial fibrosis, musculoskeletal fibrosis, post-surgical adhesions, human kidney disease (e.g., nephritic syndrome, Alport syndrome, HIV-associated nephropathy, polycystic kidney disease, Fabry's disease, diabetic nephropathy, chronic glomerulonephritis, nephritis associated with systemic lupus, and the like), progressive systemic sclerosis (PSS), primary sclerosing cholangitis (PSC), liver fibrosis, liver cirrhosis, renal fibrosis, pulmonary fibrosis, cystic fibrosis, chronic graft versus host disease, scleroderma (local and systemic), Grave's ophthalmopathy, diabetic retinopathy, glaucoma, Peyronie's disease, penis fibrosis, urethrostenosis after cystoscope, inner accretion after surgery, scarring, myelofibrosis, idiopathic retroperitoneal fibrosis, peritoneal fibrosis from a known etiology, drug-induced ergotism, fibrosis incident to benign or malignant cancer, fibrosis incident to microbial infection (e.g., viral, bacterial, parasitic, fungal, etc.), Alzheimer's disease, fibrosis incident to inflammatory bowel disease (including stricture formation in Crohn's disease and microscopic colitis), stromal cell tumors, mucositis, fibrosis induced by chemical or environmental insult (e.g., cancer chemotherapy, pesticides, or radiation (e.g., cancer radiotherapy)).

In some embodiments, the fibrosis related disorder is selected from systemic or local scleroderma, keloids, hypertrophic scars, atherosclerosis, restenosis, pulmonary inflammation and fibrosis, idiopathic pulmonary fibrosis, liver cirrhosis, fibrosis as a result of chronic hepatitis B or C infection, kidney disease, heart disease resulting from scar tissue, macular degeneration, and retinal and vitreal retinopathy. In some embodiments, the fibrosis related disorder results from chemotherapeutic drugs, radiation-induced fibrosis, and injuries and burns. In some embodiments, the fibrosis related disorder or condition results from post-surgical scarring, e.g., following trabeculectomy or other filtration surgery of the eye.

In some embodiments, the SAP-responsive disorder is a hypersensitivity disorder such as those mediated by Th1 or Th2 responses. The use of SAP as a therapeutic treatment for hypersensitivity disorders is also described in U.S. Provisional Application No. 61/209,795, which is hereby incorporated by reference. Hypersensitivity-related disorders that may be amenable to treatment with SAP include, but are not limited to, allergic rhinitis, allergic sinusitis, allergic conjunctivitis, allergic bronchoconstriction, allergic dyspnea, allergic increase in mucus production in the lungs, atopic eczema, dermatitis, urticaria, anaphylaxis, pneumonitis, and allergic-asthma.

In some embodiments, an SAP variant or SAP oligomer of the invention may be used to treat allergen-specific immune responses, such as anaphylaxis, to various antigens, including, but not limited to, antimicrobials (e.g., cephalosporins, sulfonamides, penicillin and other β-lactams), anticonvulsants (e.g., phenyloin, phenobarbital, carbamazepine, dapsone, allopurinal, and minocycline), chemotherapeutics (e.g., taxanes, platinum compounds, asparaginases, and epipodophyllotoxins), heparin, insulin, protamine, aspirin and other non-steroidal anti-inflammatory drugs, muscle relaxants (e.g., succinylcholine, atracurium, vecuronium, and pancuronium), induction agents (e.g., barbiturates, etomidate, propofol), narcotics (e.g., fentanyl, meperidine, morphine), colloids for intravascular volume expansion, radiocontrast materials, blood products, latex, animal products, animal dander, dust mites, insects (e.g., bites, stings or venom), cosmetics, metals (e.g., nickel, cobalt, and chromate), plants, spores, pollen, food (e.g., milk, eggs, wheat, soy, peanuts and tree nuts, seafood), vaccination, and fungal antigens (e.g., *Aspergillus, Curvularia, Exserohilum*, and *Alternaria* species).

In some embodiments, the SAP-responsive disorder is an autoimmune disorder such as those mediated by Th1 or Th2 responses. The use of SAP as a therapeutic treatment for autoimmune disorders is also described in U.S. Provisional Application No. 61/209,845, which is hereby incorporated by reference. Autoimmune related disorders that may be amenable to treatment with SAP include, but are not limited to, type I diabetes, multiple sclerosis, rheumatoid arthritis, psoriatic arthritis, autoimmune myocarditis, pemphigus, myasthenia gravis, Hashimoto's thyroiditis, Graves' disease, Addison's disease, autoimmune hepatitis, chronic Lyme arthritis, familial dilated cardiomyopathy, juvenile dermatomyositis, polychondritis, Sjogren's syndrome, psoriasis, juvenile idiopathic arthritis, inflammatory bowel disease, systemic lupus erythematosus, chronic obstructive pulmonary disease, and graft-versus-host disease.

In some embodiments, the SAP-responsive disorder is a mucositis. The use of SAP as a therapeutic treatment for mucositis is also described in U.S. application Ser. No. 12/217,614, which is hereby incorporated by reference. Methods of the invention may be useful for treating oral, esophageal, and gastrointestinal mucositis, as well as gastric and duodenal ulcers, or erosions of the stomach and esophagus.

In some embodiments, an SAP variant or SAP oligomer of the invention may be used to treat an inflammatory disease. In some embodiments, the inflammatory disease may be a viral, bacterial, fungal, or parasitic infection. The use of SAP as a therapeutic treatment for viral infection has also been described in U.S. Pat. No. 6,406,698 and in PCT Application WO1997/026906, which are both hereby incorporated by reference.

Pharmaceutical Preparations and Formulations

In certain aspects, the disclosure provides pharmaceutical preparations comprising one or more SAP therapeutic agents (i.e., SAP variants and SAP oligomers) formulated for administration. The therapeutic agents of the invention may be formulated in a conventional manner using one or more physiologically acceptable carriers or excipients. For example, therapeutic agents and their physiologically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In certain embodiments, therapeutic agents may be administered locally, at the site where the target cells are present, i.e., in a specific tissue, organ, or fluid (e.g., blood, cerebrospinal fluid, tumor mass, etc.).

The present invention further provides use of any SAP variant or SAP oligomer of the invention in the manufacture of a medicament for the treatment or prevention of a disorder or a condition, as described herein, in a patient, for example, the use of an SAP variant or SAP oligomer in the manufacture of medicament for the treatment of a disorder or condition described herein. In some aspects, any SAP variant or SAP oligomer of the invention may be used to make a pharmaceutical preparation for the use in treating or preventing a disease or condition described herein.

Therapeutic agents can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included. In some embodiments, the therapeutic agents can be administered to cells by a variety of methods know to those familiar in the art, including, but not restricted to, encapsulation in liposomes, by iontophoresis, or by incorporation into other vehicles, such as hydrogels, cyclodextrins, biodegradable nanocapsules, and bioadhesive microspheres.

For oral administration, the pharmaceutical compositions may take the form of, for example, tablets, lozenges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), therapeutic agents may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin, for example, for use in an inhaler or insufflator may be formulated containing a powder mix of the compound and a suitable powder base such as lactose or starch.

In the methods of the invention, the pharmaceutical compounds can also be administered by intranasal or intrabronchial routes including insufflation, powders, and aerosol formulations (for examples of steroid inhalants, see Rohatagi (1995) J. Clin. Pharmacol. 35:1187-1193; Tjwa (1995) Ann. Allergy Asthma Immunol. 75:107-111). For example, aerosol formulations can be placed into pressurized acceptable propellants, such as dichlorodifluoromethane, propane, nitrogen, and the like. They also may be formulated as pharmaceuticals for non-pressured preparations such as in a nebulizer or an atomizer. Typically, such administration is in an aqueous pharmacologically acceptable buffer.

Pharmaceutical compositions suitable for respiratory delivery (e.g., intranasal, inhalation, etc.) of variant SAP polypeptides may be prepared in either solid or liquid form.

SAP variants or SAP oligomers of the invention may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition, SAP variants or SAP oligomers of the invention may also be formulated as a depot preparation. Such long-acting formulations may be administered by implantation (for example subcutaneously or intramuscularly) or by intramuscular injection. Thus, for example, therapeutic agents may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the blood-brain-barrier in an attempt to exploit one of the endogenous transport pathways of the blood-brain-barrier); pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

In certain embodiments, SAP variants or SAP oligomers of the invention are incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Pharmaceutical compositions (including cosmetic preparations) may comprise from about 0.00001 to 100% such as from 0.001 to 10% or from 0.1% to 5% by weight of one or more of the SAP variants or SAP oligomers described herein. In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of therapeutic agents, or by insertion of a sustained release device that releases therapeutic agents. SAP variants or SAP oligomers of the invention may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, conjunctiva, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds may be injected directly into the vitreous and aqueous humour. In a further alternative, the compounds may be administered systemically, such as by intravenous infusion or injection, for treatment of the eye.

Therapeutic agents described herein may be stored in oxygen-free environment according to methods in the art.

Exemplary compositions comprise an SAP variant or SAP oligomer with one or more pharmaceutically acceptable carriers and, optionally, other therapeutic ingredients. The carrier(s) must be "pharmaceutically acceptable" in the sense of being compatible with the other ingredients of the composition and not eliciting an unacceptable deleterious effect in the subject. Such carriers are described herein or are otherwise well known to those skilled in the art of pharmacology. In some embodiments, the pharmaceutical compositions are pyrogen-free and are suitable for administration to a human patient. In some embodiments, the pharmaceutical compositions are irritant-free and are suitable for administration to a human patient. In some embodiments, the pharmaceutical compositions are allergen-free and are suitable for administration to a human patient. The compositions may be prepared by any of the methods well known in the art of pharmacy.

In some embodiments, an SAP variant or SAP oligomer is administered in a time release formulation, for example in a composition which includes a slow release polymer. An SAP variant or SAP oligomer can be prepared with carriers that will protect against rapid release. Examples include a controlled release vehicle, such as a polymer, microencapsulated delivery system, or bioadhesive gel. Alternatively, prolonged delivery of an SAP variant or SAP oligomer may be achieved by including in the composition agents that delay absorption, for example, aluminum monostearate hydrogels and gelatin.

Methods for delivering nucleic acid compounds are known in the art (see, e.g., Akhtar et al., 1992, Trends Cell Bio., 2, 139; and Delivery Strategies for Antisense Oligonucleotide Therapeutics, ed. Akhtar, 1995; Sullivan et al., PCT Publication No. WO 94/02595). These protocols can be utilized for the delivery of virtually any nucleic acid compound. Nucleic acid compounds can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, 1997, Neuroscience, 76, 1153-1158). Other approaches include the use of various transport and carrier systems, for example though the use of conjugates and biodegradable polymers. For a comprehensive review on drug delivery strategies, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400. More detailed descriptions of nucleic acid delivery and administration are provided in Sullivan et al., supra, Draper et al., PCT WO93/23569, Beigelman et al., PCT Publication No. WO99/05094, and Klimuk et al., PCT Publication No. WO99/04819.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXEMPLIFICATION

Example 1

SAP Variants Resistant to Calcium-Mediated Aggregation

Figure 1:
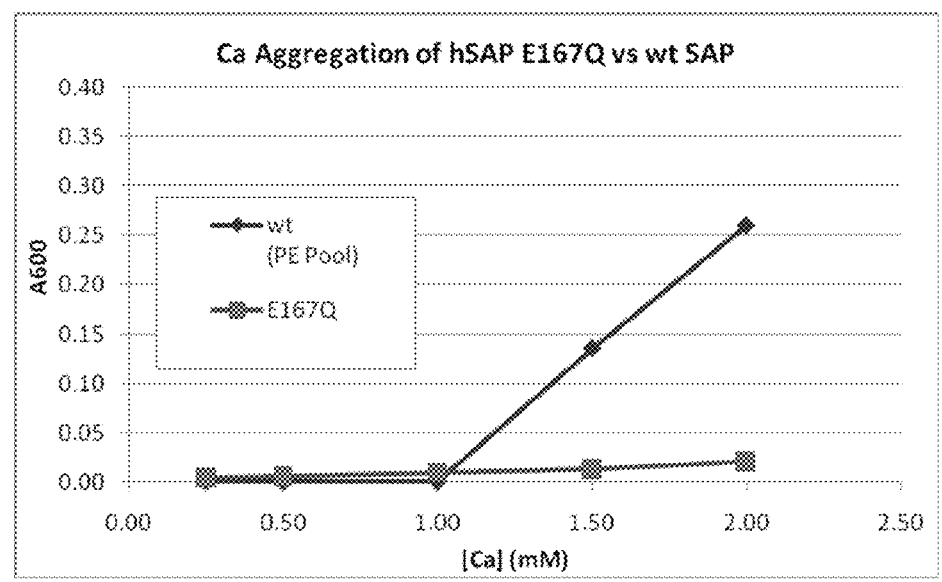
FIG. 1: An SAP variant comprising an amino acid substitution E167Q, relative to the sequence of SEQ ID NO: 1, is more resistant to calcium-mediated aggregation than a corresponding sample of unmodified recombinant human SAP (rhSAP). Incremental amounts of calcium was added a solution comprising SAP, and the amount of SAP aggregation was observed by measuring the absorbance of the solution at 600 nm in a spectrophotometer.

A recombinant human SAP (rhSAP) variant comprising an E167Q amino acid substitution, relative to the sequence of SEQ ID NO: 1, was expressed in CHO cells and purified from the CHO cell culture media. The calcium-mediated aggregation of the rhSAP variant was then compared to that of a corresponding sample of wild-type rhSAP. Incremental amounts of calcium was added to either a solution of rhSAP variant E167Q or wild-type rhSAP (each at a SAP concentration of 4.4 mg/mL), and the amount of SAP aggregation was observed by measuring the absorbance of the solution at 600 nm in a spectrophotometer. FIG. 1 demonstrates that the rhSAP variant E167Q is significantly more resistant to calcium-mediated aggregation that the wild-type rhSAP.

Figure 2:
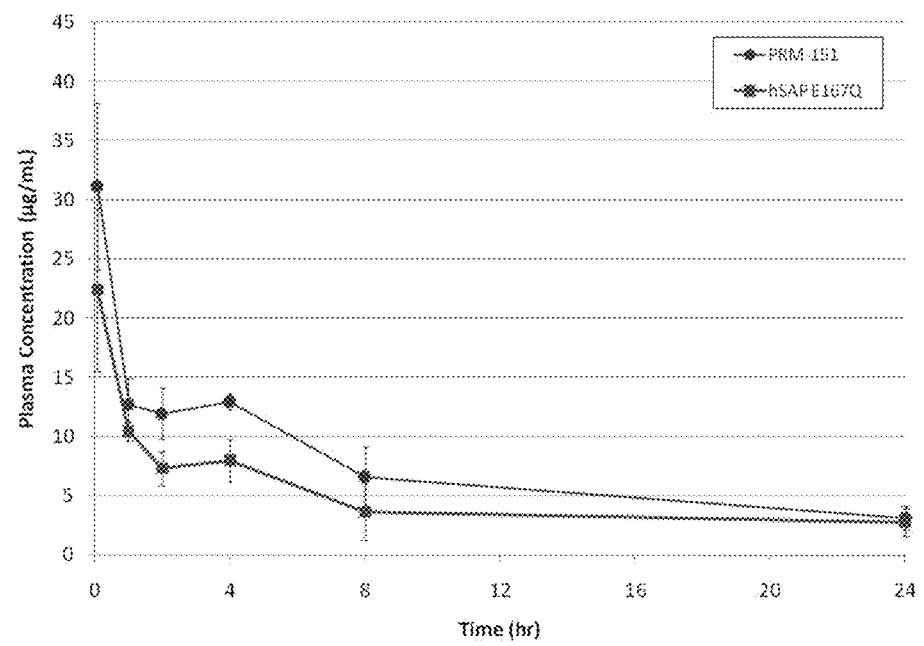
FIG. 2: An SAP variant comprising an amino acid substitution E167Q, relative to the sequence of SEQ ID NO: 1, has a similar plasma half-life compared to a corresponding sample of unmodified recombinant human SAP (rhSAP). Rats were administered SAP (1 mg/kg i.v. does per rat, n=3).

The pharmacokinetics (PK) of the rhSAP variant E167Q was also compared to a corresponding sample of wild-type rhSAP. Rats were administered (1 mg/kg i.v. dose per rat, n=3) either the rhSAP variant E167Q or a corresponding sample of wild-type rhSAP. Over the next twenty-four hours, the rats were assessed for plasma concentration (μg/mL) of SAP protein. FIG. 2 demonstrates that the rhSAP variant E167Q has a similar plasma half-life to that of wild-type rhSAP.

In a further experiment, an in vitro bioassay was used to determine the relative activity of the rhSAP variant E167Q. In this assay, monocyte-enriched Peripheral Blood Mononuclear Cells (PBMCs) were incubated with varying concentrations of either the rhSAP variant E167Q or hSAP for 96 hours. Following this incubation, the resulting culture supernatants were removed and assayed by ELISA to quantify the amount of Macrophage Derived Chemokine (MDC) that was produced. MDC is produced by fibrocytes and therefore an indicator of monocyte differentiation into fibrocytes. By comparing the inhibitory concentration, 50% ($IC_{50}$) of the sample to the hSAP reference standard, the relative potency of a SAP variant can be determined. The result is expressed as an $IC_{50}$ ratio of the sample versus the hSAP reference standard.

All SAP samples and standards were initially diluted to a concentration of 1.0 mg/mL in Supplemented FibroLife Media. SAP standards were serially diluted to generate working standard concentrations of 60, 30, 20, 13.4, 8.8, 6.0, 3.0, 1.5, and 0.75 μg/mL (final standard concentration of 30, 15, 10, 6.7, 4.4, 3.0. 1.5, 0.75, and 0.375 μg/mL). See the following Table 1.

| Working rhSAP Standard Concentration (μg/mL) | Volume of Standard | Volume of Supplemented FibroLife Media |
|---|---|---|
| 60 | 60 (1 mg/mL) | 940 |
| 30 | 600 (60 μg/mL) | 600 |
| 20 | 800 (30 μg/mL Std) | 400 |
| 13.4 | 800 (20 μg/mL Std) | 400 |
| 8.8 | 800 (13.4 μg/mL Std) | 400 |
| 6.0 | 800 (8.8 μg/mL Std) | 400 |
| 3.0 | 600 (6.0 μg/mL Std) | 600 |
| 1.5 | 600 (3.0 μg/mL Std) | 600 |
| 0.75 | 600 (1.5 μg/mL Std) | 600 |

To prepare for the ELISA assay, the Capture Antibody (i.e., mouse anti-human MDC) was diluted to the working concentration in PBS without carrier protein. The diluted capture antibody was used to coat 96-well plates, and then each plate was sealed and incubated overnight at room temperature. Before using the coated plates, each well was aspirated and washed with Wash Buffer, repeating the process two times for a total of three washes. The plates were then blocked by adding 300 μL, of Reagent Diluent to each well and incubating at room temperature for one hour. After incubation the aspiration and well-washing procedure was repeated.

For the ELISA assay, 100 μL, samples of either the supernatants from the monocyte/fibrocyte cultures or the SAP standards were added to each well. The plate was then incubated at room temperature for 2 hours before aspirating and washing the wells. Then 100 μL, of a working dilution of Streptavidin-HRP was added to each well. The plate was incubated for 20 minutes at room temperature before adding 50 μL, of Stop Solution to each well. Immediately, the optical density of each well was measured using a microplate reader set to 450 nm. If wavelength correction was available, the microplate reader was set to 540 nm or 570 nm. If wavelength correction was not available, then the readings at 540 nm or 570 nm were subtracted from the readings at 450 nm. This subtraction corrects for optical imperfections in the plate.

FIG. 3 demonstrates that rhSAP variant E167Q is at least as biologically active as wild-type rhSAP.

Example 2

Deglycosylated SAP Variants have Altered Plasma Half-Life and Biological Activity A recombinant human SAP (rhSAP) variant comprising an N32D amino acid substitution, relative to the sequence of SEQ ID NO: 1, was expressed in CHO cells and purified from the CHO cell culture media. This mutation disrupts an N-glycosylation consensus site and thereby prevents attachment of N-linked glycans to SAP at that position. In parallel, wild-type hSAP was treated with a sialidase to remove all sialic acid moieties attached to the SAP polypeptide (i.e., asialo hSAP). Both the untreated rhSAP N32D and asialo hSAP were compared with a corresponding sample of rhSAP in a PK assay to measure for in vivo serum stability (FIG. 4). While the PK of the rhSAP N32D was slightly reduced compared to wild-type SAP, the half-life of the rhSAP N32D was substantially higher than that of the asialo hSAP. The rhSAP N32D variant was further compared to a corresponding sample of serum-derived hSAP using an in vitro bioassay to determine the relative activity of these proteins (FIG. 3). These data indicate that the N32D SAP variant maintains a plasma half-life and activity comparable to wild-type hSAP.

Example 3

Covalent Attachment of PEG to SAP

A recombinant human SAP (rhSAP) variant was covalently attached to a 20 kDa activated methoxyPEG derivative (PEG). The PEG moiety was attached to a primary amine group of rhSAP according to the following protocol and as illustrated in FIG. 5. First, approximately 1 mg of 20 kDa methoxy-PEG-succinimidyl-carboxymethyl ester (Jen-Kem cat# M-SCM-20K) per mg of rhSAP was dissolved in a 20 mg/mL solution of rhSAP. The coupling reaction was allowed to proceed for 24 hours at room temperature. The resulting pegylated-rhSAP was purified from reaction components by anion exchange chromatography. Fractions from the chromatography column were pooled and concentrated (FIG. 6). PEGylated rhSAP made by this procedure contained from 1-3 20 kDa PEGs/protomer, with 1 PEG/protomer being the most abundant form, as assessed by SDS-PAGE.

The PEGylated rhSAP and human serum-derived SAP (hSAP) were assayed for bioactivity using an in vitro bioassay. In this assay, monocyte enriched Peripheral Blood Mononuclear Cells (PBMCs) were incubated with varying concentrations of either PEGylated rhSAP or hSAP for 96 hours. Following this incubation, resulting culture supernatants were removed and assayed by ELISA to quantify the amount of Macrophage Derived Chemokine (MDC) that was produced. MDC is produced by fibrocytes and therefore an indicator of monocyte differentiation into fibrocytes. By comparing the inhibitory concentration, 50% ($IC_{50}$) of the sample to the hSAP reference standard, the relative potency of a SAP variant can be determined. The result is expressed as an $IC_{50}$ ratio of the sample versus the hSAP reference standard as described in the preceding examples.

The PEGylated rhSAP variant was had an $IC_{50}$ ratio of 0.24 compared to a corresponding sample of hSAP, thereby demonstrating that the PEGylated rhSAP has comparable activity to wild-type SAP.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will be apparent to those skilled in the art upon review of this specification and the below-listed claims. The full scope of the invention should be determined by reference to the claims, along with their full scope of equivalents, and the specification, along with such variations.

I claim:

1. A pharmaceutical composition comprising a Serum Amyloid P (SAP) variant comprising five SAP protomers, wherein each of the SAP protomers have an amino acid sequence at least 95% identical to SEQ ID NO: 1, and wherein all five SAP protomers comprise an amino acid at position 167 of SEQ ID NO: 1 that is not E, and a pharmaceutically acceptable ophthalmic vehicle.

2. The pharmaceutical composition of claim 1, wherein the SAP variant is more resistant to calcium-dependent autoaggregation than a corresponding sample of non-variant human SAP.

3. The pharmaceutical composition of claim 1 or 2, wherein each of the SAP protomers has an amino acid sequence that is at least 96% identical to SEQ ID NO: 1.

4. The pharmaceutical composition of claim 1, wherein each of the SAP protomers has an amino acid sequence that is at least 97% identical to SEQ ID NO: 1.

5. The pharmaceutical composition of claim 1, wherein each of the SAP protomers has an amino acid sequence that is at least 98% identical to SEQ ID NO: 1.

6. The pharmaceutical composition of claim 1 or 2, wherein each of the SAP protomers has an amino acid sequence that is at least 99% identical to SEQ ID NO: 1.

7. The pharmaceutical composition of claim 1, wherein at least one of the SAP protomers comprises an aspartate (D), asparagine (N), glutamine (Q), alanine (A), or histidine (H) at position 167 of SEQ ID NO: 1.

8. The pharmaceutical composition of claim 7, wherein at least one of the SAP protomers comprises a glutamine (Q) at position 167 of SEQ ID NO: 1.

9. The pharmaceutical composition of claim 2, wherein the pharmaceutical composition is suitable for administration by intraocular injection.

10. The pharmaceutical composition of claim 1, wherein each of the SAP protomers comprises an aspartate (D), asparagine (N), glutamine (Q), alanine (A), or histidine (H) at position 167 of SEQ ID NO: 1.

11. The pharmaceutical composition of claim 10, wherein each of the SAP protomers comprises a glutamine (Q) at position 167 of SEQ ID NO: 1.

12. A method for treating macular degeneration, retinal or vitreal retinopathy, fibrosis related disorder or condition following trabeculectomy or other filtration surgery of the eye, Grave's ophthalmopathy, diabetic retinopathy, or glaucoma, the method comprising administering to a patient in need thereof the pharmaceutical composition of claim 2.

13. The method of claim 12, wherein the method is a method for treating macular degeneration.

14. The method of claim 12, wherein the pharmaceutical composition is administered by intraocular injection.

15. A method for treating a fibrotic or fibroproliferative disorder, the method comprising administering to an eye of a patient in need thereof the pharmaceutical composition of claim 2.

16. A method for treating an inflammatory disease, the method comprising administering to an eye of a patient in need thereof the pharmaceutical composition of claim 2.

17. A method for treating macular degeneration, retinal or vitreal retinopathy, fibrosis related disorder or condition following trabeculectomy or other filtration surgery of the eye, Grave's ophthalmopathy, diabetic retinopathy, or glaucoma, the method comprising administering to a patient in need thereof the pharmaceutical composition of claim 11.

18. The method of claim 17, wherein the method is a method for treating macular degeneration.

19. A method for treating a fibrotic or fibroproliferative disorder, the method comprising administering to an eye of a patient in need thereof the pharmaceutical composition of claim 11.

20. A method for treating an inflammatory disease, the method comprising administering to an eye of a patient in need thereof the pharmaceutical composition of claim 11.

* * * * *